US007297354B2

(12) United States Patent
Miller et al.

(10) Patent No.: US 7,297,354 B2
(45) Date of Patent: Nov. 20, 2007

(54) PROTEIN MATERIAL

(75) Inventors: Bill L. Miller, Fort Dodge, IA (US); Mary R. Higgins, Fridley, MN (US); Madhu Kakade, Roseville, MN (US); Tim Emerson, Churchville, NY (US); Jane Kitchar, Elkhart, IN (US); Christopher S. Penet, Henrietta, NY (US)

(73) Assignees: Land O'Lakes, Inc., Arden Hills, MN (US); Genencor International, Inc., Palo Alto, CA (US)

( * ) Notice: Subject to any disclaimer, the term of this patent is extended or adjusted under 35 U.S.C. 154(b) by 66 days.

(21) Appl. No.: 10/240,049

(22) PCT Filed: Apr. 26, 2001

(86) PCT No.: PCT/US01/13372

§ 371 (c)(1),
(2), (4) Date: Mar. 11, 2003

(87) PCT Pub. No.: WO01/80665

PCT Pub. Date: Nov. 1, 2001

(65) Prior Publication Data

US 2003/0211202 A1    Nov. 13, 2003

Related U.S. Application Data

(60) Provisional application No. 60/199,758, filed on Apr. 26, 2000.

(51) Int. Cl.
*A23L 1/20* (2006.01)
(52) U.S. Cl. .......................... 426/46; 426/52; 435/68.1
(58) Field of Classification Search ................ 426/46, 426/49, 52, 56; 435/68.1
See application file for complete search history.

(56) References Cited

U.S. PATENT DOCUMENTS

| 3,640,725 A | 2/1972 | Sherba et al. .................. 99/17 |
| 3,761,353 A | 9/1973 | Noe et al. ...................... 195/29 |
| 3,857,966 A | 12/1974 | Feldman et al. ............... 426/7 |
| 3,928,630 A | 12/1975 | Perini ............................ 426/7 |
| 3,953,611 A | 4/1976 | Youngquist ................... 426/93 |
| 4,036,993 A | 7/1977 | Ikeda et al. ..................... 426/7 |
| 4,054,677 A | 10/1977 | Orban ........................ 426/602 |
| 4,100,024 A | 7/1978 | Adler-Nissen ............... 195/29 |
| 4,107,334 A | 8/1978 | Jolly .............................. 426/7 |
| 4,266,031 A | 5/1981 | Tang et al. .................. 435/188 |
| 4,293,571 A | 10/1981 | Olofsson et al. ............... 426/7 |
| 4,302,473 A | 11/1981 | Mikami et al. ............... 426/46 |
| 4,324,805 A | 4/1982 | Olsen .......................... 426/46 |
| 4,368,151 A | 1/1983 | Howard et al. .......... 260/123.5 |
| 4,378,376 A | 3/1983 | Wagner et al. ............... 426/41 |
| 4,409,256 A | 10/1983 | Johnson et al. ............. 426/598 |
| 4,443,540 A | 4/1984 | Chervan et al. .............. 435/69 |
| 4,473,589 A | 9/1984 | Freeman et al. ............... 426/7 |
| 4,477,472 A * | 10/1984 | Seto et al. ..................... 426/98 |
| 4,482,574 A | 11/1984 | Lee .............................. 426/7 |
| 4,760,025 A | 7/1988 | Estell et al. ................ 435/222 |
| 4,771,126 A | 9/1988 | Hirotsuka et al. .......... 530/378 |
| 4,882,180 A | 11/1989 | Takao et al. ................ 426/46 |
| 5,077,062 A | 12/1991 | Ernster ....................... 426/46 |
| 5,082,672 A | 1/1992 | Hamada et al. ............... 426/7 |
| 5,100,679 A | 3/1992 | Delrue ........................ 426/44 |
| 5,155,033 A | 10/1992 | Estell et al. ................ 435/221 |
| 5,185,258 A | 2/1993 | Caldwell et al. ............ 435/220 |
| 5,270,200 A | 12/1993 | Sun et al. ................ 435/240.2 |
| 5,273,773 A | 12/1993 | Katayama et al. .......... 426/656 |
| RE34,606 E | 5/1994 | Estell et al. ................ 435/222 |
| 5,346,823 A | 9/1994 | Estell et al. ................ 435/222 |
| 5,356,637 A | 10/1994 | Loosen et al. ................. 426/7 |
| 5,565,225 A | 10/1996 | Johnston ....................... 426/2 |
| 5,618,689 A | 4/1997 | McCarthy et al. ......... 435/68.1 |

(Continued)

FOREIGN PATENT DOCUMENTS

EP    0 072 617    10/1986

(Continued)

OTHER PUBLICATIONS

Lallès, J.P., Plumb, G.W., Mills, E.N.C., Morgan, M.R.A. Tukur, H.M., and Toullec, R., *Antigenic Activity of Some Soyabean Products Used in Veal Calf Feeding: Comparison Between In Vitro Tests (ELISA Polyclonal vs. Monoclonal) And With In Vivo Data*, pp. 281-285 in van der Poel, A.F.B., Huisman, J., and Saini, H.S., ed., *Recent Advances of Research in AntiNutritional Factors in Legume Seeds*, Publ. No. 70 (1993 Washington Pers, Wageningen, The Netherlands).

Tukur, H.M., Lallès, J.P., Mathis, C., Caugant, I., and Toullec, R., *Digestion of Soybean Globulins, Glycinin, α-conglycinin and β-conglycinin, in the Preruminant and the Ruminant Calf*, Can. J. Anim. Sci., vol. 73, pp. 891-905 (Dec. 1993).

Lallès, J.P.; Tukur, H.M.; Toullec, R.; and Miller, B.G., *Analytical Criteria for Predicting Apparent Digestibility of Soybean Protein in Preruminant Calves*, J. Dairy Sci., vol. 79, pp. 475-482 (1996).

Tukur, H. M.; Lalles, J. P.; Plumb, G. W.; Mills, E. N. C.; Morgan, M. R. A.; and Toullec, R., *Investigation of the Relationship Between in Vitro ELISA Measures of Immunoreactive Soy Globulins and in Vivo Effects of Soy Products*, Journal of Agricultural and Food Chemistry, vol. 44, pp. 2155-2161 (1996).

(Continued)

*Primary Examiner*—Arthur L. Corbin
(74) *Attorney, Agent, or Firm*—Westman, Champlin & Kelly, P.A.; Z. Peter Sawicki

(57) ABSTRACT

A method of treating a proteinaceous material having a first concentration of β-conglycinin, the method including combining the proteinaceous material with an enzyme to form a reaction mixture, the reaction mixture initially having a pH of at least about 7.0 standard pH units, allowing the enzyme to hydrolyze β-conglycinin present in the reaction mixture to form a proteinaceous intermediate, and inactivating the enzyme present in the reaction mixture after a reaction period to form a proteinaceous product, the proteinaceous product having a second concentration of β-conglycinin, the second concentration of β-conglycinin being at least 99 percent less than the first concentration of β-conglycinin.

31 Claims, 4 Drawing Sheets

U.S. PATENT DOCUMENTS

| | | | |
|---|---|---|---|
| 5,674,700 A | 10/1997 | Maurel | 435/7.94 |
| 5,700,676 A | 12/1997 | Bott et al. | 435/221 |
| 5,763,257 A | 6/1998 | Bott et al. | 435/221 |
| 5,801,038 A | 9/1998 | Bott et al. | 435/221 |
| 5,922,373 A | 7/1999 | Johnston | 426/2 |
| 5,945,299 A | 8/1999 | von Kries et al. | 435/68.1 |
| 5,955,340 A | 9/1999 | Bott et al. | 435/221 |
| 5,972,682 A | 10/1999 | Bott et al. | 435/221 |
| 6,007,851 A | 12/1999 | Schoenmaker et al. | 426/46 |
| 6,024,990 A | 2/2000 | Kofoed et al. | 426/44 |
| 6,036,983 A | 3/2000 | Nielsen | 426/53 |
| 6,096,353 A | 8/2000 | Meheus et al. | 426/53 |
| 6,126,973 A | 10/2000 | Tsumura et al. | 426/44 |
| 6,159,715 A | 12/2000 | Porter et al. | 435/170 |
| 6,171,640 B1 | 1/2001 | Bringe | 426/656 |
| 6,190,900 B1 | 2/2001 | Sierkstra et al. | 435/221 |
| 6,190,904 B1 | 2/2001 | Amory et al. | 435/264 |
| 6,303,178 B1 | 10/2001 | Tsumura et al. | 426/654 |
| 2001/0024677 A1 | 9/2001 | Bringe | 426/656 |

FOREIGN PATENT DOCUMENTS

| | | |
|---|---|---|
| EP | 0 313 274 | 4/1989 |
| EP | 0 320 717 | 6/1989 |
| EP | 0 407 981 | 1/1994 |
| EP | 0 501 117 | 1/1996 |
| EP | 0 797 927 | 10/1997 |
| EP | 0 925 723 | 6/1999 |
| EP | 0 797 928 | 11/1999 |
| EP | 0 522 800 | 1/2001 |
| GB | 1 443 160 | 7/1976 |
| WO | WO 88/09933 | 12/1988 |
| WO | WO 89/06091 | 7/1989 |
| WO | WO 90/01023 | 2/1990 |
| WO | WO 97/01965 | 1/1997 |
| WO | WO 97/44664 | 11/1997 |
| WO | WO 98/00508 | 1/1998 |
| WO | WO 98/44807 | 10/1998 |
| WO | WO 00/19839 | 4/2000 |

OTHER PUBLICATIONS

Lalles, J.P., Tukur, H.M., Salgado, P., Mills, E.N.C., Morgan, M.R.A., Quillien, L., Levieux, D., and Toullec, R., *Immunochemical Studies on Gastric and Intestinal Digestion of Soybean Glycinin and β-conglycinin in Vivo*, Journal of Agricultural and Food Chemistry, vol. 47, pp. 2797-2806 (Jul. 1999).

Lalles J.P.; Tukur H.M.; and Toullec, R., Abstract of *Immunochemical Tests for the Determination of Glycinin and β-conglycinin Levels in Soya Products for Calf Milk Replacers*; Protein Metabolism And Nutrition: Proceedgins of the 7th International Symposium on Protein Metabolism and Nutrition; EAAP Publication, vol. 81; pp. 243-244; Editors: A. F. Nunes, A. V. Portugal, J.P. Costa and J. R. Riberio; BIOSIS No. 199699169689; May 24-27, 1995.

Tukur, H.M.; Pardal, P.B.; Formal, M.; Toullec, R.; Lalles, J.P.; and Guilloteau, P.; *Digestibility, Blood Levels of Nutrients and Skin Responses of Calves Fed Soyabean and Lupin Proteins*, Reproduction Nutrition Development; vol. 35; pp. 27-44 (1995).

Heppell, L.M. J.; Sissons, J.W.; and Pedersen, H.E., *A Comparison of the Antigenicity of Soya-bean-based Infant Formulas*, British Journal of Nutrition, vol. 58 (3), pp. 393-404 (1987).

Sissons, J. W. and Thurston, S. M., *Survival of Dietary Antigens in the Digestive Tract of Calves Intolerant to Soyabean Products*, Research in Veterinary Science, vol. 37, pp. 242-246 (1984).

Sissons, J. W.; Nyrup, A.; Kilshaw, P.J.; and Smith, R.H., *Ethanol Denaturation of Soya Bean Protein Antigens*, Journal of the Science of Food and Agriculture, vol. 33; pp. 706-710 (1982).

Kilshaw, P.J. and Sissons, J.W., *Gastrointestinal Allergy to Soyabean Protein in Preruminant Calves. Allergenic Constituents of Soyabean Products*, Research in Veterinary Science, vol. 27; pp. 366-371 (1979).

Bush, R.S.; Toellec, R.; Caugant, I.; and Guilloteau, P., *Effects of Raw Pea Flour on Nutrient Digestibility and Immune Responses in the Preruminant Calf*, J. Dairy Sci., vol. 75, pp. 3539-3552 (1992).

Montagne, L.; Toullec, R.; and Lalles, J.P., *Calf Intestinal Mucin; Isolation, Partial Characterization, and Measurement in Ileal Digesta With an Enzyme-Linked Immunosorbent Assay*, J. Dairy Science, vol. 83, pp. 507-517 (2000).

Perez, M.D,; Mills, E.N.C.; Lambert, N.; Johnson, I.T.; and Morgan, M.R.A., *The Use Of Anti-Soya Globulin Antisera In Investigating Soya Digestion In Vivo*, Journal of the Science of Food and Agriculture, vol. 80, pp. 513-521(2000).

Lalles, J.P.; Toullec, R.; and Pardal, P.B., *Hydrolyzed Soy Protein Isolate Sustains High Nutritional Performance In Veal Calves*, J. Dairy Science, vol. 78, pp. 194-204 (1995).

Lalles, J.P., *Soy Products as Protein Sources For Preruminants and Young Pigs*, Proceedings of the World Soybean Research Conference VI, pp. 106-126 (Aug. 4-7, 1999).

Koshiyama, I.; Kikuchi, M.; Harada, K.; and Fukushima, D, *2S Globulins Of Soybean Seeds, 1. Isolation and Characterization of Protein Components*; J. Agric. Food Chem., vol. 29, pp. 336-340 (1981).

Christensen, D., *Enzymes: A New Approach To Enhancing Ruminant Rations*, Feed News, vol. 2, issue 2, three pages (published by The Signature Group, 608 Duchess Street, Saskatoon, Saskatchewan, Canada S7K 0R1) (Spring, 1997).

Harwood, C.R. (Editor), Biotechnology Handbook (2): *Bacillus*, pp. 295-297, ISBN 0-306-43137-8 (Plenum Press, New York, 1989).

Sonenshein, A.L.; Hoch, J.A.; and Losick, R. (Editors), *Bacillus Subtilis and Other Gram-Positive Bacteria: Biochemistry, Physiology and Molecular Genetics*; pp. 9 and 938-952; ISBN 1-55581-053-5 (American Society For Microbiology; 1993).

Product Information Sheet for Alcalase® Food Grade Enzyme of Novo Nordisk A/S; Four pages; Jul. 1998.

Emerson, T.; Penet, C.; and Gerstner, J.; Abstract of *Enzymatic Treatment of Low-PDI Soy Products For Enhanced Physical Properties*; one page, distributed at Annual Meeting of American Oil Chemical Society in San Diego, California, (Apr. 26, 2000).

Material Safety Data Sheet by Canada Colors and Chemicals Limited For Multifect P3000 Enzyme, 4 pages (Jul. 9, 1999).

White, J.S. and White, D.C.; *Source Book of Enzymes*; pp. 569-571 (CRC Press, New York, 1997).

Meira, L., *Enzimas*, nine pages, [retrieved on Apr. 1, 2001]. Retrieved from the Internet: <URL: http://www.geocities.com/HotSprings/2220/enzimas,htm>.

Rose, A.H. (Editor), *Economic Microbiology, Volume 5: Microbial Enzymes and Bioconversions*; pp. 49-115, ISBN 0-12-596555-9 (Academic Press, London, 1980).

Terui, G. (Editor), Fermentation Technology Today: Proceedings of the IVth International Fermentation Symposium; Kyoto, Japan; pp. 283-305 (Society of Fermentation Technology, Japan, 1972).

Kumar, C.G. and Takagi, H., *Microbial Alkaline Proteases, From A Bioindustrial Viewpoint*, Biotechnology Advances, vol. 17, issue 7, pp. 561-594 (Dec. 15, 1999) [retrieved on Apr. 20, 2001]. Retrieved from the Internet via <URL: http://www.sciencedirect.com>.

van der Poel, A.F.B, Huisman, J., and Saini, H.S., *Proceedings of the Second International Workshop on 'Antinutritional Factors (ANFs) in Legume Seeds': Recent Advances of Research in Antinutritional Factors In Legume Seeds*; pp. v-x; EAAP Publication No. 70 (Wageningen, The Netherlands, 1993).

Jansman, A.J.M.; Hill, G.D.; van der Poel, A.F.B, *Proceedings of the Third International Workshop on 'Antinutritional Factors (ANFs) in Legume Seeds': Recent Advances of Research in Antinutritional Factors In Legume Seeds and Rapeseeds*; Table of Contents (six page list of articles); EAAP Publication No. 93 (Wageningen, The Netherlands, 1998).

Drackley, J.K., *Soy In Animal Nutrition*, Table of Contents: pp. vii-viii (Federation of Animal Science Societies—Aug. 4-5, 1999).

Heppell, L.M.J., *Determination of Milk Protein Denaturation by an Enzyme-linked Immunosorbent Assay*, pp. 115-123 of Morris, B.A. and Clifford, M.N., *Immunoassays in Food Analysis*, ISBN 0-85334-321-7 (Elsevier Science Publishing Co. New York, New York, 1985).

Toullec, R., Lalles, J.P., and Tukur, H.M., *Relationships Between Some Characteristics of Soybean Products and Nitrogen Apparent Disgestibility in Preruminant Calves*, pp. 229-232 of the Proceedings of the First Meeting of the Institut National de la Recherche Agronomique: ("Rencontres autour des recherches sur les ruminants"), ISBN: 2-84148-004-6 (Paris, France, Dec. 1-2, 1994).

Lalles, J.P.; Tukur, H.M.; and Toullec, R., *Assessment of the Antigenicity of Soya Products for Calf Milk Replacers: Which Immunochemical Tests to Use?*, p. 135 of the Proceedings of the Second Meeting of the Institut National de la Recherche Agronomique: ("Rencontres autour des recherches sur les ruminants"), ISBN: 2-84148-016-X (Paris, France, Dec. 13-14, 1995).

Lalles, J.P. and Toullec, R., Abstract of *Soybean Products in Milk Replacers for Farm Animals: Processing, Digestion, and Adverse Reactions*, Recent Research Developments in Agricultural & Food Chemistry, vol. 2, No. 2, pp. 565-576 (1998).

Lalles, J.P., Heppell, L.M.J., Sissons, J.W., and Toullec, R., Abstract of *Antigenicity of Dietary Protein From Soyabean Meal and Peas in the Dairy CalfThroughout Weaning*; Reproduction, Nutrition,Development, vol. 31, No. 3, p. 303 (1991).

Dreau, D.; Larre, C.; and Lalles, J.P.; Abstract of *Semi-Quantitative Purification and Assessment of Purity of Three Soybean Proteins—Glycinin, BETA-conglycinin, and ALPHA-conglycinin—by SDS-PAGE electrophoresis, densitometry and Immunoblotting*, Journal of Food Science and Technology, vol. 31, pp. 489-493 (1994).

Lallès, J.P., Tukur, H.M., Dréau, D. and Toullec, R., *Contribution of INRA to the Study of Antigenicity of Plant Protein Used in Young Farm Animal Nutrition*. In: Van Oort, M.G. and Tolman, G.H.: Antigenicity of Legume Proteins. TNO Communications. 25 pp (1992).

Lalles, J.P.; Tukur, H.M.; and Toullec, R., *Immunochemical Tests for Measuring Glycinin and Beta-conglycinin Concentrations in Soyabean Products Predictive Value for Nitrogen Digestibility and Soyabean Immunogenicity in the Calf*, Annales de Zootechnie (Paris), 46 (3), pp. 193-205 (1997). CAB Accession No. 981400459, BIOSIS No. 199799684390.

Toullec, R.; Lalles, J. P.; and Tukur, H.M., *Biochemical Characteristics and Apparent Digestibility of Nitrogen in Soyabeans in Pre-ruminant Calves* (Original Title: Caracteristiques Biochimiques et Digestibilite Apparente Des Matieres Azotees De Soja Chez Le Veau Preruminant), ISBN: 2-84148-004-6, pp. 229-232, (1994 Institut de l'Elevage, Paris, France).

Toullec, R.; Lalles, J. P.; and Tukur, H.M., *Biochemical Characteristics and Apparent Digestibility of Nitrogen in Soyabeans in Pre-ruminant Calves* (Original Title: Caracteristiques Biochimiques et Digestibilite Apparente Des Matieres Azotees De Soja Chez Le Veau Preruminant), ISBN: 2-84148-004-6, pp. 229-232, (1994 Institut de l'Elevage, Paris, France).

Lalles, J.P., Tukur, H.M., and Toullec, R., *Assessment of the Antigenicity of Soya Products for Calf Milk Replacers: Which Immunochemical Tests to Use?(Evaluation De L'antigenicite Des Produits du Soja Destines Aux Aliments D'allaitement Pour Veaux: Quels Tests Immunochimiques Utiliser?)*, p. 135 in Proceedings of the 2nd meeting " Rencontres Autour Des Recherches Sur Les Ruminants" of the Institut National de la Recherche Agronomique, held in Paris (France), on Dec. 13 and 14 of 1995. (Dec. 1995, Institut de l'Elevage, Paris, France), ISBN: 2-84148-016-X.

Toullec, R., Lalles, J.P., and Tukur, H.M., *Relationships Between Some Characteristics of Soybean Products and Nitrogen Apparent Digestibility in Preruminant Calves (Caracteristiques Biochimiques et Digestibilite Apparente Des Matieres Azotees De Soja Chez Le Veau Preruminant)*, pp. 229-232 of the Proceedings of the first meeting "Rencontres autour des recherches sur les ruminants". of the Institut National de la Recherche Agronomique, held in Paris (France), on Dec. 1 and 2 of 1994, (Dec. 1994, Institut de l'Elevage, Paris, France), ISBN: 2-84148-004-6.

Lalles, J. P. and Toullec, R., *Soybean Products in Milk Replacers for Farm Animals: Processing, Digestion and Adverse Reactions*, CAB Accession No. 991411987; no date noted.

Lalles, J. P., Heppell, L.M.J., Sissons, J.W., and Toullec, R., *Antigenicity of Dietary Protein from Soyabean Meal and Peas in the Dairy Calf Throughout Weaning*, CAB Accession No. 920451145; no date noted.

Dreau, D., Larre, C., and Lalles, J. P. *Semi-quantitative Purification and Assessment of Purity of Three Soybean Proteins—Glycinin, Beta-conglycinin and Alpha-conglycinin—by Sds-page Electrophoresis, Densitometry and Immunoblotting*, Journal of Food Science and Technology, India, vol. 31 (6), pp. 489-493 (1994), ISSN: 0022-1155.

Heppell, L.M.J., *Determination of milk protein Denaturation by an Enzyme-Linked Immunosorbent Assay*, pp. 115-123 in Morris, B.A. and Clifford, M.N., eds., Immunoassays in Food Analysis (1985 Elsevier Applied Science publishers, London, England).

* cited by examiner

PROTEIN MATERIAL

CROSS-REFERENCE TO RELATED APPLICATION(S)

This application claims the benefit of priority from U.S. patent application Ser. No. 60/199,758 that was filed on Apr. 26, 2000 and also claims the benefit of priority from PCT International Application Ser. No. PCT/US01/13372 that was filed on Apr. 26, 2001, since this application is a National Phase application into the U.S. filed under 35 U.S.C. § 371 from PCT International Application Ser. No. PCT/US01/13372 that was filed on Apr. 26, 2001 and since PCT International Application Ser. No. PCT/US01/13372 claims the benefit of priority from U.S. Provisional Application Ser. No. 60/199,758 that was filed on Apr. 26, 2000.

BACKGROUND OF THE INVENTION

The present invention generally relates to a method of reducing the antigenicity of vegetable proteins, while also improving the solubility characteristics of the vegetable proteins. More particularly, the present invention relates to a method of enzymatically hydrolyzing vegetable proteins, such as raw, natural soy proteins and denatured soy proteins, to reduce the antigenicity of the vegetable proteins while also improving the solubility characteristics of the vegetable proteins.

Over the years, researchers have found that soybeans may be processed to recover or extract a number of valuable components, such as soy protein and soybean oil, from the soy beans. Also, soybeans may be processed to form soy flours high in nutritionally beneficial substances, such as fiber and protein. Such processing of soybeans often include heat treatment for a variety of purposes, such as inactivating destructive enzymes or inactivating compounds responsible for off-flavors that are unpalatable to humans and/or animals.

Soybean processing techniques that employ heat frequently cause denaturation of proteins present in resulting soy component and products. The degree of protein denaturation depends upon the duration of heat and the temperature profile during the heating, among other factors. Additionally, some proteins in soybeans are more susceptible to denaturation at particular heating conditions than are other soybean proteins. Nonetheless, denaturation of soy proteins is problematic since denatured proteins typically exhibit greatly diminished solubility in water and aqueous solutions.

Many soy products, such as soy flour, soy flakes, and soy meal, are available and are commonly used for production of animal feeds and food products for human consumption. However, any such soy products that have been heat processed to a substantial degree have also undergone substantial soy protein denaturation and, consequently, frequently have a Protein Dispersability Index (subsequently referred to as "PDI") on the order of about 20 or even less. The PDI is a measure of protein solubility (and consequently a measure of protein dispersability) in water. The PDI decreases as the level of protein denaturation in a soy component or product increases, absent further processing of the denatured protein to enhance the solubility of the denatured protein. Though there are vegetable protein products with relative high PDIs of 90 or more, and thus high levels of soluble proteins, these products are typically very expensive and/or often contain high levels of antigenic proteins.

Heat treating of soybeans and soybean components, although beneficial for deactivating destructive enzymes and compounds that contribute to unpalatable tastes, nevertheless do little, if anything, to reduce the antigenicity of the heat-processed soybean products. The antigenicity of a particular substance is directly correlated to the concentration of antigens present in the substance. Glycinin and $\beta$-conglycinin, which are commonly referred to as antigenic proteins, are two proteins in soybean products that cause the majority of the antigenicity typically observed in soybean products. Consequently, glycinin and $\beta$-conglycinin, by their presence or absence, predominantly control the level of antigenicity of a particular soybean product.

Heat-treating and heat-processing typically do not sufficiently reduce the concentration of antigenic proteins, such as glycinin and $\beta$-conglycinin, in a particular proteinaceous material. Other soybean processing techniques exist that may or may not incorporate heat treatment steps. For example, some commercial processing plants employ organic solvents, such as hexane, to extract oil from soy beans or soy products, such as soy flakes. The heat that is applied during the oil extraction process causes some denaturation of protein in the soy products. The heat is typically employed during the oil extraction process for purposes of evaporating the organic solvent. This heating for solvent evaporation purposes may cause some reduction of the antigenic protein concentration, though any such reduction is only an insignificant reduction. The organic solvent, such as hexane, that is employed in these processes for oil extraction purposes typically does not cause the destruction or removal of antigenic proteins, such as glycinin and $\beta$-conglycinin. There are other organic solvents that may be employed in these processes for purposes other than oil extraction. Some of these other organic solvents may even bring about significant reductions of the concentration of antigenic proteins, such as glycinin and $\beta$-conglycinin, in a particular proteinaceous material.

The destruction of antigenic protein that provides a reduced level of antigenicity in soybean products is important, since antigens, such as antigenic proteins, when introduced into a human being or into an animal, frequently cause production of antibodies that lead to development of allergic reactions that in turn reduce the digestibility of soybean products or cause other nutritional disturbances. Thus, to reduce the opportunity for allergic reactions, it is beneficial to reduce the antigenicity of soybean products by reducing the concentration of antigenic proteins, such as glycinin and $\beta$-conglycinin, in the soybean products.

However, soybean processing techniques that rely on organic solvents, even though beneficial for destruction of antigenic proteins, are not an optimum solution to the antigenicity issue. First, reducing the antigenicity of soybean products using such solvent-based processing techniques nevertheless typically leaves the soybean products with high levels of denatured proteins. These high levels of denatured proteins contribute to poor protein solubility characteristics in soybean products produced by solvent-based processing techniques. Furthermore, complete removal of the organic solvent from soybean products produced by solvent-based processing techniques is challenging and often incomplete, since trace levels of the organic solvent typically remain in the soybean product. Consumers are increasingly aware of research studies that raise questions about the effects of trace levels of organic solvents on human health. Therefore, to raise public perception of food quality, it is useful to minimize or even eliminate use of organic solvents in food processing techniques.

However, other than solvent-based processing techniques, heat-based processing techniques that denature proteins while leaving antigenic proteins intact or substantially intact are the most common soybean processing techniques. Furthermore, other processing techniques, such as grinding or milling, though not relying upon heating that denatures proteins, nevertheless, typically leave high and substantial levels of antigenic protein in the processed soybean components.

Thus, there is a need in the food and animal feed manufacturing industries for a technique of processing vegetable protein sources, such as soybeans and soybean components, that reduces the antigenicity in soybean products to reduce the potential for allergic reactions in humans and animals that consume the soybean products. Furthermore, there is a need for a food and animal feed processing technique that improves the solubility, and thus the dispersability, of denatured proteins in vegetable sources of protein, such as soybean products. Enhanced solubility and dispersability of denatured proteins is necessary to allow production of beverages, such as milk substitutes, milk replacers, and infant formulas, that contain proteins derived from vegetable sources, such as soybeans, and to support production of food products and animal feeds that incorporate dispersed or emulsified proteins derived from vegetable sources, such as soybeans. The process of the present invention provides an optimum solution to these needs by providing a product with proteins exhibiting high levels of solubility where the product also contains minimal, if any, levels of antigenic proteins.

BRIEF SUMMARY OF THE INVENTION

The present invention includes a method of treating a proteinaceous material having a first concentration of β-conglycinin. The method includes combining the proteinaceous material with an enzyme to form a reaction mixture, the reaction mixture initially having a pH of at least about 7.0 standard pH units, allowing the enzyme to hydrolyze β-conglycinin present in the reaction mixture to form a proteinaceous intermediate, and inactivating the enzyme present in the reaction mixture after a reaction period to form a proteinaceous product. The proteinaceous product produced by the method has a second concentration of β-conglycinin that is at least 99 percent less than the first concentration of β-conglycinin. The present invention also includes a method of treating a proteinaceous material, a method of treating a proteinaceous material having a first concentration of glycinin, and a method of treating a proteinaceous material having a first Protein Dispersability Index.

DETAILED DESCRIPTION

Figure 1:
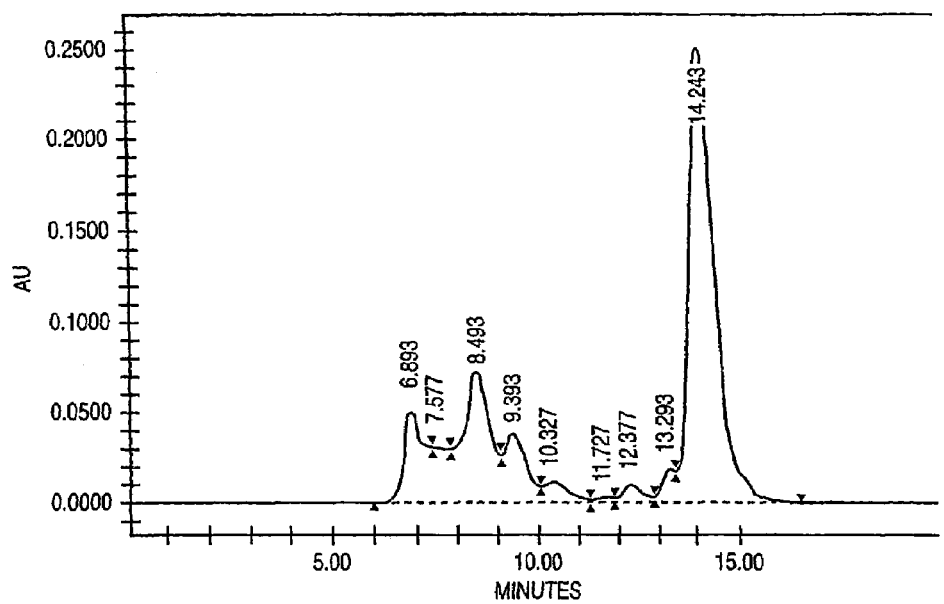
FIG. 1 is a size distribution plot of protein fragments with different molecular weights present in a vegetable protein source that was used as feed material in the process of the present invention.

The present invention generally relates to a method of reducing the antigenicity of vegetable proteins, while also improving the solubility characteristics of the vegetable proteins. More particularly, the present invention relates to a method of enzymatically hydrolyzing vegetable proteins, such as raw, natural soy proteins and denatured soy proteins, to reduce the antigenicity of the vegetable proteins while also improving the solubility characteristics of the vegetable proteins.

Briefly, the process of the present invention entails the formation of an aqueous slurry of one or more vegetable protein materials to form a slurried vegetable protein feed. The slurried vegetable protein feed is subjected to the action of a protease (a "proteolytic enzyme") to produce a slurried vegetable protein product. The pH of the slurried vegetable protein feed and the temperature of the slurried vegetable protein feed that are selected such that action of the protease on proteins present in the slurried vegetable protein feed is effective (1) to enhance the level of protein solubility in the slurried vegetable protein product, as compared to the level of protein solubility in the slurried vegetable protein feed, and (2) to reduce the level of antigenicity in the slurried vegetable protein product, as compared to the level of antigenicity in the slurried vegetable protein feed. Preferably, the slurried vegetable protein feed, at an alkaline pH, is subjected to the action of an alkaline proteolytic enzyme at a temperature of about 60° C. or less, to produce the slurried vegetable protein product. The slurried vegetable protein product, after preparation, is then heated to inactivate the proteolytic enzyme and is thereafter dried to form a powdered vegetable protein product of the present invention.

The process of the present invention may be beneficially employed to hydrolyze proteins from any source, such as vegetable protein materials, animal protein materials, marine protein materials, and any combination of any of these. Some examples of vegetable protein materials are protein materials derived from soybeans, such as soy protein isolate, toasted or untoasted soy flour, soy grits, soy flakes, soy meal, soy protein concentrates, and any combination of any of these. The vegetable protein material, such as any of the soybean protein sources listed above, maybe defatted, reduced fat, or full fat vegetable protein materials. Some examples of animal protein materials include egg albumin isolate; powdered egg whites; dairy protein materials, such as whey protein isolate, whey protein concentrate, and powdered whey; and any combination of any of these. As with the vegetable protein materials, any animal protein material(s) may be defatted, reduced fat, or full fat in nature. Some examples of marine protein materials include protein-containing materials derived from marine creatures, such as fish. As with the vegetable protein materials and the animal protein materials, any marine protein material(s) may be defatted, reduced fat, or full fat in nature.

Though descriptions of the present invention are primarily made in terms of vegetable protein material, it is to be understood that any other protein material, such as animal protein materials and marine protein materials, may be substituted in place of vegetable protein material, in accordance with the present invention, while still realizing benefits of the present invention. Likewise, it is to be understood that any combination of any protein material, such as any combination of vegetable protein material, animal protein materials, and/or marine protein materials, may be processed in accordance with the present invention, while still realizing benefits of the present invention.

The slurried vegetable protein feed may be prepared by combining the vegetable protein material with water. While the total solids concentration in the slurried vegetable protein feed is not critical to the present invention, the total solids concentration in the slurried vegetable protein feed preferably ranges between about 10 weight percent and about 35 weight percent, based upon the total weight of the slurried vegetable protein feed. Total solids concentrations higher than about 35 weight percent are less desirable because such higher concentrations increase the viscosity of the slurried vegetable protein feed and consequently may cause difficulties in preparing, mixing and/or handling the slurried vegetable protein feed. Total solids concentrations lower than about 10 weight percent in the slurried vegetable protein feed are less preferred, because such lower total solids concentrations would increase the size of equipment needed to accomplish the process of the present invention and would ultimately require removal of greater amounts of moisture to produce the powdered vegetable protein product of the present invention.

After preparation, the temperature of the slurried vegetable protein feed is adjusted to a temperature where action of the protease on proteins present in the slurried vegetable protein feed is effective (1) to enhance the level of protein solubility in the slurried vegetable protein product, as compared to the level of protein solubility in the slurried vegetable protein feed, and (2) to reduce the level of antigenicity in the slurried vegetable protein product, as compared to the level of antigenicity in the slurried vegetable protein feed. Preferably, when the protease is an alkaline proteolytic enzyme, the slurried vegetable protein feed is heated to a temperature of about 60° C., or less, such as to a temperature of about 50° C. to about 60° C.

The slurried vegetable protein feed may be held in a batch reactor, such as a tank or other vessel that is jacketed for circulation of steam, hot water, or other heating fluid to attain and maintain the desired temperature, such as the preferred temperature of about 60° C., or less. Alternatively, the slurried vegetable protein feed may be circulated from the batch reactor, through a heat exchanger, and back into the batch reactor to heat the slurried vegetable protein feed. As another alternative, the water that is blended with the vegetable protein material to form the slurried vegetable protein feed maybe heated prior to combination of the vegetable protein material and the water. The batch reactor containing the slurried vegetable protein feed should be equipped with an agitator that is capable of maintaining the homogeneity of the slurried vegetable protein feed during preparation, pH adjustment, and enzymatic hydrolysis.

After the slurried vegetable protein feed has been heated to the desired temperature, such as the preferred temperature of about 60° C., or less, an alkaline agent or an acidic agent, as appropriate, is added to adjust the pH of the slurried vegetable protein feed. The pH of the slurried vegetable protein feed is adjusted to a pH that is within the range of pHs where action of the protease on proteins present in the slurried vegetable protein feed is effective (1) to enhance the level of protein solubility in the slurried vegetable protein product, as compared to the level of protein solubility in the slurried vegetable protein feed, and (2) to reduce the level of antigenicity in the slurried vegetable protein product, as compared to the level of antigenicity in the slurried vegetable protein feed.

After the slurried vegetable protein feed has been heated to the desired temperature, such as the preferred temperature of about 60° C., or less, the alkaline agent is preferably added to adjust the pH of the slurried vegetable protein feed to a pH of about 7.0 standard pH units, or more, such as to a pH of about 7.0 standard pH units to about 10.0 standard pH units, since the activity of one preferred alkaline proteolytic enzyme is improved within this pH range. More preferably, the pH of the slurried vegetable protein feed is adjusted to a pH of about 8.5 standard pH units, or more, such as to a pH of above about 8.5 standard pH units to a pH of about 9.5 standard pH units, since the enzymatic hydrolysis reaction has been observed to enhance protein solubility and/or minimize antigenicity levels when the pH of the slurried vegetable protein feed is adjusted to this more preferred range. Still more preferably, the pH of the slurried vegetable protein feed is adjusted to a pH ranging from about 9.0 standard pH units to about 9.5 standard pH units, such as at a pH of about 9 standard pH units, since the enzymatic hydrolysis reaction has been observed to enhance protein solubility and/or minimize antigenicity levels when the pH of the slurried vegetable protein feed is adjusted to this level.

The alkaline agent is preferably an edible, food grade alkaline agent. Some examples of suitable edible, food grade, alkaline agents include sodium hydroxide, potassium hydroxide, calcium hydroxide, and magnesium hydroxide. Typically, any alkaline agent that is used will be in the form of an aqueous solution of the alkaline agent, such as an alkaline, aqueous solution containing about 10 weight percent of the alkaline agent in water, based upon the total weight of the aqueous solution, to minimize the potential for over-shooting the desired pH of the slurried vegetable protein feed.

The acidic agent is preferably an edible, food grade acidic agent. Some examples of suitable edible, food grade, acidic agents include hydrochloric acid and acetic acid. Typically, any acidic agent that is used will be in the form of an aqueous solution of the acidic agent, such as an acidic, aqueous solution containing about 10 weight percent of the acidic agent in water, based upon the total weight of the aqueous solution, to minimize the potential for over-shooting the desired pH of the slurried vegetable protein feed.

After preparation and pH adjustment of the slurried vegetable protein feed, the slurried vegetable protein feed is hydrolyzed to cleave proteins of the slurried vegetable protein feed into protein fragments (peptides) with smaller molecular weights than the proteins of the slurried vegetable protein feed and to reduce the concentration of antigenic proteins, such as glycinin and β-conglycinin, originally present in the slurried vegetable protein feed. The hydrolysis maybe achieved in a single stage enzymatic hydrolysis reaction that employs one or more proteolytic enzymes. Preferably, the one or more proteolytic enzymes are one or more alkaline proteolytic enzymes.

When the preferred alkaline proteolytic enzyme(s) is employed, the enzymatic hydrolysis reaction begins with the slurried vegetable protein feed at a pH of about 7.0 standard pH units, such as at a pH of about 7.0 standard pH units to about 10.0 standard pH units; more preferably with the slurried vegetable protein feed at a pH of about 8.5 standard pH units, or more, such as at a pH above about 8.5 standard pH units to about 9.5 standard pH units; more preferably with the slurried vegetable protein feed at a pH within the range of from about 9.0 standard pH units to about 9.5 standard pH units, such as at a pH of about 9 standard pH units. After the enzymatic hydrolysis reaction begins, the pH of the slurried vegetable protein feed is thereafter preferably allowed to freely change, without any subsequent pH adjustment or pH control. Changes in the pH of the slurried vegetable protein feed are thought to be caused by the enzymatic hydrolysis reaction.

As an optional alternative, as the enzymatic hydrolysis reaction progresses, the pH of the slurried vegetable protein feed may be adjusted or controlled to remain within the pH range or at the pH of the slurried vegetable protein feed that existed upon initiation of the enzymatic hydrolysis reaction. Preferably, however, such adjustment or control of the pH is not done during the enzymatic hydrolysis reaction because (1) such pH adjustment or control may require additional labor and/or equipment, (2) such pH adjustment or control does not significantly affect (a) the beneficial protein solubility enhancement or (b) the beneficial antigenicity reduction that are achieved by the process of the present invention. Furthermore, such pH adjustment or control does not significantly affect the rates at which the beneficial protein solubility enhancement or the beneficial antigenicity reduction are achieved by the process of the present invention minimization. However, despite not needing to control pH during the enzymatic hydrolysis reaction, the temperature of the slurried vegetable protein feed within the batch reactor is maintained at the desired reaction temperature, such as the preferred reaction temperature of about 60° C., or less, and agitation is maintained to maintain homogeneity of the contents of the batch reactor during the enzymatic hydrolysis reaction.

Following addition of the proteolytic enzyme, such as the preferred alkaline proteolytic enzyme, the enzymatic hydrolysis reaction is allowed to proceed at the selected temperature, such as the preferred temperature of about 60° C., or less, for a period of time that is effective to modify the proteinaceous components of the slurried vegetable protein feed in accordance with the present invention and to the desired degree. Though those of ordinary skill in the art will recognize that this period of time may vary, depending upon the particular proteolytic enzyme(s) employed, the activity of the proteolytic enzyme(s), the temperature of the slurried vegetable protein feed at the onset of, and during, the enzymatic hydrolysis reaction, and other factors, this period of time will, nevertheless, typically range from about 5 minutes to 120 minutes.

Enzymes that are capable of hydrolyzing proteins are commonly referred to as carbonyl hydrolases. In addition to hydrolyzing peptide bonds of proteins, carbonyl hydrolases, depending upon the conditions, are often capable of hydrolyzing peptide bonds of peptides, ester bonds of fatty acids, and ester bonds of triglycerides. As used herein, a protein generally consists of at least about ten individual amino acids, whereas a peptide, which is a protein fragment, generally consists of about two to about nine individual amino acids. There are both naturally-occurring forms of carbonyl hydrolases and recombinant forms of carbonyl hydrolases. Some of the more important types of naturally-occurring carbonyl hydrolases include, for example, lipases, proteases, such as subtilisins and metalloproteases, and peptide hydrolases. Some non-exhaustive examples of peptide hydrolases include alpha-amino acylpeptide hydrolase, peptidyl-amino acid hydrolase, acylamino acid hydrolase, serine carboxypeptidase, metallocarboxypeptidase, thiol proteinase, carboxyl proteinase and metalloproteinase. Some non-exhaustive exemplary classes of proteases may further include thiol, acid, endo, and exo proteases.

A recombinant carbonyl hydrolase is a carbonyl hydrolase that is not naturally-occurring. A naturally-occurring carbonyl hydrolase is encoded with a naturally-occurring DNA sequence. In a recombinant carbonyl hydrolase, the DNA sequence that would ordinarily encode the carbonyl hydrolase has been modified into a mutant, or non-naturally-occurring, DNA sequence. The mutant DNA sequence encodes a substitution, insertion, and/or deletion of one or more amino acids in the amino acid sequence that would ordinarily be present in the naturally-occurring carbonyl hydrolase. Thus, the presence of the mutant DNA sequence, namely an amino acid sequence not found in nature, causes the carbonyl hydrolase that includes the DNA sequence to be a non-naturally-occurring, or recombinant, carbonyl hydrolase. The precursor carbonyl hydrolase of any particular recombinant carbonyl hydrolase may itself be either a naturally-occurring carbonyl hydrolase or a recombinant carbonyl hydrolase. Suitable methods for modifying the amino acid sequence to yield a recombinant carbonyl hydrolase are disclosed in U.S. Pat. Nos. 5,185,258; 5,204,015; 5,700,676; 5,763,257; 5,801,038; and 5,955,350 and in PCT Publication Nos. WO 95/10615 and WO 99/20771.

Enzymes that are capable of hydrolyzing proteins may also be known as proteases, and enzymes that are capable of hydrolyzing peptides may also be known as peptide hydrolases. Proteases may also be referred to as proteolytic enzymes. Proteases are a form of carbonyl hydrolases that, under suitable conditions, may cleave peptide bonds of proteins, whereas peptide hydrolases are a form of carbonyl hydrolases that under suitable conditions, may cleave peptide bonds of peptides. Some proteases, under suitable conditions, may also cleave peptide bonds of peptides, and thus may also be characterized as peptide hydrolases. Therefore, a peptide hydrolase may also be a protease. On the other hand, a protease is not necessarily a peptide hydrolase, though some proteases are in fact peptide hydrolases.

Proteases, like carbonyl hydrolases, may be either naturally-occurring proteases with naturally-occurring DNA sequences or recombinant proteases with mutant DNA sequences. Likewise, peptide hydrolases, like carbonyl hydrolases, may be either naturally-occurring peptide hydrolases with naturally-occurring DNA sequences or recombinant hydrolases with mutant DNA sequences.

Recombinant proteases and recombinant peptide hydrolases may be directly derived from naturally-occurring proteases and naturally-occurring peptide hydrolases), respectively (i.e.: when the recombinant protease or recombinant peptide hydrolase is a mutant of the naturally-occurring protease or the naturally-occurring peptide hydrolase, respectively). Also, recombinant proteases and recombinant peptide hydrolases may be indirectly derived from naturally-occurring proteases and naturally-occurring peptide hydrolases), respectively (where the recombinant protease or recombinant peptide hydrolase is a second order relative of the naturally-occurring protease or the naturally-occurring peptide hydrolase, respectively, i.e.: when a first recombinant protease or first recombinant peptide hydrolase is a mutant of a second recombinant protease or a second recombinant peptide hydrolase, respectively, and the second recombinant protease or the second recombinant peptide hydrolase is a mutant of the naturally-occurring protease or the naturally-occurring peptide hydrolase, respectively).

Naturally-occurring proteases (and naturally-occurring peptide hydrolases) are available from many sources, including animal, vegetable, and microbial matter. Recombinant proteases and recombinant peptide hydrolases may be directly or indirectly derived from naturally-occurring proteases and naturally-occurring peptide hydrolases, respectively, with any source, such as an animal, vegetable, or microbial source. Naturally-occurring proteases from any source, such as an animal, vegetable, or microbial source, maybe employed in the process of the present invention, and recombinant proteases that are directly or indirectly derived from naturally-occurring proteases and naturally-occurring peptide hydrolases, respectively, from any source, such as an animal, vegetable, or microbial source, may be employed in the process of the present invention.

Trypsin and chymotrypsin, which are each pancreatic proteases, are some non-exhaustive examples of suitable naturally-occurring proteases from animal matter that may be employed in the process of the present invention. Ficin, bromelain, and papain are some non-exhaustive examples of suitable naturally-occurring proteases from vegetable matter that may be employed in the process of the present invention. *Bacillus* spp., i.e.: *Bacillus licheniformis, Bacillus subtilis, Bacillus alkalophilus, Bacillus cereus, Bacillus natto*, and *Bacillus vulgatus*, which are each bacterial proteases, and *Aspergillus* spp., *Mucor* spp., and *Rhizopus* spp., which are each examples of fungal proteases, are some non-exhaustive examples of suitable naturally-occurring microbial proteases that may be employed in the process of the present invention.

A serine protease is a protease that includes a catalytic triad of three particular amino acids, namely aspartate, histidine, and serine. Like the more general protease classification, some serine proteases, under appropriate conditions, act as peptide hydrolases that cleave peptide linkages of peptides and are consequently also properly classified as serine peptide hydrolases. Both naturally-occurring serine proteases and recombinant serine proteases may be employed in the process of the present invention. Preferably, any naturally-occurring serine proteases and any recombinant serine proteases that are employed in the process of the present invention also act as serine peptide hydrolases under the conditions employed in the process of the present invention.

A couple of exemplary serine proteases are subtilisins and chymotrypsins. Subtilisins are microbial proteases, and, more specifically, have both fungal and bacterial origins. On the other hand, chymotrypsins are pancreatic enzymes with an animal origin. In the subtilisins, the relative order of the catalytic triad of amino acids (aspartate, histidine, and serine), reading from the amino to carboxy terminus of the triad, is aspartate-histidine-serine. In the chymotrypsins, the relative order of the catalytic triad of amino acids (aspartate, histidine, and serine), reading from the amino to carboxy terminus of the triad, is, however, histidine-aspartate-serine. Thus, a subtilisin is a serine protease that has the catalytic triad of amino acids arranged in the aspartate-histidine-serine order. Naturally-occurring or recombinant subtilisins may be employed in the process of the present invention. Preferably, any naturally-occurring or recombinant subtilisin that is employed in the process of the present invention also acts as a peptide hydrolase under the conditions employed in the process of the present invention.

Bacillus subtilisins are subtilisin proteases with a microbial origin. Like the more general protease classification, some bacillus subtilisins, under appropriate conditions, act as peptide hydrolases that cleave peptide linkages of peptides and are consequently also properly characterized as bacillus subtilisin peptide hydrolases. Both naturally-occurring bacillus subtilisins and recombinant bacillus subtilisins may be employed in the process of the present invention. Preferably, any naturally-occurring bacillus subtilisins and any recombinant bacillus subtilisins that are employed in the process of the present invention also act as bacillus subtilisin peptide hydrolases under the conditions employed in the process of the present invention.

A series of naturally-occurring bacillus subtilisins is known to be produced and secreted by various microbial species, such as *B. amyloliquefaciens, B. licheniformis, B. subtilis,* and *B. pumilus*, for example. Though the amino acid sequences of the members of this naturally-occurring bacillus subtilisin series are not entirely homologous, the subtilisins in this series tend to exhibit the same or similar type of proteolytic activity, though stability issues do exist for some members of this series. Also, conditions for satisfactory activity levels vary somewhat between some members of this series. Furthermore, it is believed that some members of this series exhibit strong peptide hydrolase activity, whereas other members of this series exhibit little if any peptide hydrolase activity. The exemplary bacillus subtilisins provided above may be divided into two groups: (1) the subtilisins secreted by *B. licheniformis* (subtilisin Carlsberg) and *B. pumilus*, which are generally less stable below a pH of about 9.0 and (2) the subtilisins secreted by *B. amyloliquefaciens* (subtilisin Novo; subtilisin BPN) and by *B. subtilis*. Both naturally-occurring subtilisins secreted by *B. licheniformis, B. amyloliquefaciens,* and *B. subtilis*, as well as, recombinant subtilisins that are directly or indirectly derived from any of these naturally-occurring subtilisins may be employed in the process of the present invention.

In one preferred form, a recombinant subtilisin that is obtained through recombinant means is employed as the proteolytic enzyme in the process of the present invention. As used herein, the term "recombinant subtilisin" refers to a subtilisin in which the DNA sequence encoding the subtilisin is modified to produce a mutant DNA sequence that encodes the substitution, deletion, and/or insertion of one or more amino acids in the naturally-occurring subtilisin amino acid sequence that would otherwise exist. As one non-exhaustive example, the recombinant subtilisin may have methionine substituted at amino acid residues 50, 124, and 222 in place of phenylalanine, isoleucine, and glutamine, respectively.

Recombinant methods to obtain genes that encode either naturally-occurring precursor subtilisins or recombinant precursor subtilisins are known in the art. The methods generally entail synthesizing labeled probes with putative sequences that encode regions of the protease of interest, preparing genomic libraries from organisms expressing the protease of interest, and screening the libraries for the gene of interest by hybridization to the labeled probes. Positively hybridizing clones are then mapped and sequenced.

The identified protease gene is then ligated into a high copy number plasmid. The high copy number plasmid with the ligated protease gene is then used to transform a host cell and express the protease of interest. This plasmid replicates in hosts in the sense that the plasmid contains the well-known elements necessary for plasmid replication: (1) a promoter operably linked to the gene of interest (which may be supplied as the gene's own homologous promoter if the promoter is recognized, i.e., transcribed by the host), (2) a transcription termination and polyadenylation region (necessary for stability of the mRNA transcribed by the host from the protease gene in certain eucaryotic host cells) that is exogenous or is supplied by the endogenous terminator region of the protease gene, and, desirably, (3) a selection gene, such as an antibiotic resistance gene, that enables continuous cultural maintenance of plasmid-infected host cells by growth in antibiotic-containing media. High copy number plasmids also contain an origin of replication for the host that thereby enables large numbers of plasmids to be generated in the cytoplasm without chromosomal limitations. However, it is within the scope of the present invention to integrate multiple copies of the protease gene into a host genome. This is facilitated by procaryotic and eucaryotic organisms that are particularly susceptible to homologous recombination.

The following cassette mutagenesis method may also be used to facilitate construction of subtilisin variants (recombinant forms of subtilisin) that may be employed in the process of the present invention, although other methods known to those of ordinary skill in the art may also be used. First, the naturally-occurring gene encoding the subtilisin is obtained and sequenced in whole or in part. Then, the sequence is scanned for a point at which mutation (deletion, insertion, and/or substitution) of one or more amino acids in the encoded enzyme is desired. The amino acid sequences flanking this desired mutation point are evaluated for the presence of restriction sites that support replacement of a short segment of the gene with an oligonucleotide pool that, when expressed, will encode various mutants. Such restriction sites are preferably unique sites within the protease gene to facilitate replacement of the gene segment. However, any convenient restriction site that is not overly redundant in the protease gene may be used, provided the gene fragments generated by restriction digestion may be reassembled in proper sequence. If restriction sites are not present at locations within a convenient distance from the desired mutation point (from 10 to 15 nucleotides), suitable restriction sites are generated by substituting nucleotides in the gene without causing a change in either the reading frame or the amino acids that are encoded in the final construction.

Mutation of the gene to change the sequence of the gene and conform to the desired sequence is accomplished by M13 primer extension in accordance with generally known methods. The task of locating suitable flanking regions and evaluating the needed changes to arrive at two convenient restriction site sequences is made routine by the redundancy of the genetic code, a restriction enzyme map of the gene, and the large number of different restriction enzymes. Note that if a convenient flanking restriction site is available, the above method need be used only in connection with the flanking region that does not contain a site.

The gene may be naturally-occurring gene, a variant of a naturally-occurring gene, or a synthetic gene. A synthetic gene encoding a naturally-occurring or mutant precursor subtilisin may be produced by determining the DNA and/or amino acid sequence of a precursor subtilisin. Multiple, overlapping, synthetic single-stranded DNA fragments are thereafter synthesized, which upon hybridization and ligation produce a synthetic DNA encoding the precursor protease. An example of a synthetic gene construction is set forth in Example 3 of U.S. Pat. No. 5,204,015. The entire disclosure of U.S. Pat. No. 5,204,015 is therefore incorporated herein by reference.

As one non-exhaustive example, a bacillus subtilisin such as *B. amyloliquefaciens* subtilisin, which is an alkaline bacterial protease, may be mutated by modifying the DNA encoding the *B. amyloliquefaciens* subtilisin to encode the substitution of one or more amino acids of various amino acid residues within the mature form of the recombinant subtilisin product. These mutant subtilisins have at least one property that is different when compared to the same property of the precursor subtilisin. Properties that may be modified fall into several categories: oxidative stability, substrate specificity, thermal stability, alkaline stability, catalytic activity, pH activity profile, resistance to proteolytic degradation, $K_m$, kcat and $K_m$ over kcat ratio.

Though extended discussion is provided herein about alkaline proteases that may be derived from *B. amyloliquefaciens*, it is to be understood that any other alkaline protease, such as alkaline proteases of *Aspergillus* sp., *Dendryphiella* sp., *Scolebasidium* sp., *Candida lipolytica*, *Yarrowia lipolytica*, *Aureobasidium pullulans*; *Streptomyces* sp., like *Strepomyces rectus* var. *proteolyticus* NRRL 3150, *Streptomyces* sp. YSA-130, *S. diastaticus* SS1, *S. corchorusii* ST36, *S. pactum* DSM 40530; alkalophilic actinomycetes, such as *Nocardiopsis dassonvillei*, and *Oerskovia xanthineolytica* TK-1; *Pseudomonas aeruginosa*, *Pseudomonas maltophila*, or *Pseudomonas* sp. Strain B45; *Xanthomonas maltophil*; *Vibrio alginolyticus*, or *Vibrio metschnikovii* strain RH530; *Kurthia spiroforme*; *Psilotoredo healdi*; Halophiles, such as *Halobacterium* sp., like *Halobacterium halobium* ATCC 43214, or *Halomonas* sp. ES-10, may be employed in the process of the present invention to realize benefits of the present invention.

The alkaline proteolytic enzyme that is employed in the process of the present invention is preferably a bacterial alkaline proteolytic enzyme. More preferably, the bacterial alkaline proteolytic enzyme is derived from a genetically modified strain of bacteria belonging to the species *subtilis* of the genus *Bacillus*. Still more preferably, the bacterial alkaline proteolytic enzyme belongs to the species *amyloliquefaciens* of the genus *Bacillus*. Even more preferably, the bacterial alkaline proteolytic enzyme belongs to the species *amyloliquefaciens* of the genus *Bacillus* that is expressed by a genetically modified strain of bacteria belonging to the species *subtilis* of the genus *Bacillus*. As one suitable example, the alkaline proteolytic enzyme may be the alkaline proteolytic enzyme present in the MULTIFECT® P-3000 enzyme composition that is available from Genencor International, Inc. of Santa Clara, Calif.

The enzyme of the MULTIFECT® P-3000 enzyme composition is a bacterial alkaline proteolytic enzyme that belongs to the species *amyloliquefaciens* of the genus *Bacillus* and is expressed by a genetically-modified strain of bacteria belonging to the species *subtilis* of the genus *Bacillus*. The enzyme of the MULTIFECT® P-3000 enzyme composition is commonly known as a subtilisin. The MULTIFECT® P-3000 enzyme composition includes the bacterial alkaline proteolytic enzyme, along with a carrier (propylene glycol) that is compatible with the bacterial alkaline proteolytic enzyme. The MULTIFECT® P-3000 enzyme composition may be combined with the slurried vegetable protein feed at any concentration that is effective to modify the proteinaceous components of the slurried vegetable protein feed in accordance with the present invention. As one non-exhaustive example, the MULTIFECT® P-3000 enzyme composition may be combined with the slurried vegetable protein feed at a ratio ranging from about ½ pound (about 227 grams) of the MULTIFECT® P-3000 enzyme composition per 100 pounds (45.35 kilograms) of vegetable protein material to about two pounds (about 907 grams) of the MULTIFECT® P-3000 enzyme composition per 100 pounds (45.35 kilograms) of vegetable protein material.

Though extended discussion is provided herein about proteases that may be derived from specific sources, it is to be understood that proteases, generally, such as naturally-occurring proteases from any source (including, for example, an animal, vegetable, or microbial source) may be employed in the process of the present invention, and recombinant proteases that are directly or indirectly derived from naturally-occurring proteases and naturally-occurring peptide hydrolases, respectively, from any source (including, for example, an animal, vegetable, or microbial source) may be employed in the process of the present invention. Also, naturally-occurring serine proteases and recombinant serine proteases may be employed in the process of the present invention.

Additionally, naturally-occurring or recombinant subtilisins maybe employed in the process of the present invention.

Furthermore, both naturally-occurring bacillus subtilisins and recombinant bacillus subtilisins maybe employed in the process of the present invention. Likewise, both naturally-occurring subtilisins secreted by *B. licheniformis*, *B. amyloliquefaciens*, and *B. subtilis*, as well as, recombinant subtilisins that are directly or indirectly derived from any of these naturally-occurring subtilisins may be employed in the process of the present invention.

Preferably, any naturally-occurring proteases and any recombinant proteases that are employed in the process of the present invention, no matter the source or derivation of the naturally-occurring proteases and any recombinant proteases, also act as peptide hydrolases under the conditions employed in the process of the present invention.

As used herein, proteolytic activity is defined as the rate of hydrolysis of peptide bonds per milligram of active enzyme. Many well known procedures exist for measuring proteolytic activity (K. M. Kalisz, "Microbial Proteinases," Advances in Biochemical Engineering/Biotechnology, A. Fiechter ed., 1988). Techniques to determine such activities are well known in the art and may be used in the present invention for determining an appropriate concentration of protease to be employed in the process of the present invention.

Determining the optimum conditions for operation of a protease are routine for a worker of ordinary skill in the art. Through routine methods, it is possible to determine the working pH range, the optimum pH, the working temperature range, the optimum temperature range and the presence of cofactors and enzyme activators necessary to obtain suitable performance from the protease for the given task. In general, if a certain set of conditions are necessary for a particular application, it is possible to select a protease which has optimal activity under those conditions. Subtilisins are generally active in the alkaline range, i.e., at pHs greater than about 7 standard pH units, and at temperatures from about 10° C. to about 80° C.

The alkaline proteolytic enzyme(s) incorporated in the process of the present invention may be characterized as a protease that exhibits proteolytic activity at alkaline pHs, such as at a pH of about 7 standard pH units, or more. The specific level of activity of the alkaline proteolytic enzyme(s) should be effective to modify the proteinaceous components of the slurried vegetable protein feed in accordance with the present invention. Consequently, the process of the present invention is not limited to any particular level of activity of the alkaline proteolytic enzyme(s).

Following enzymatic hydrolysis of the slurried vegetable protein feed to form the slurried vegetable protein product, the proteolytic enzyme, such as the preferred alkaline proteolytic enzyme, is deactivated by heating the slurried vegetable protein product to a temperature of at least about 85° C., or more, for a period of at least about one to about two minutes, or more, preferably for a period of about 5 minutes, or more, and more preferably for a period of about 5 minutes to about 10 minutes. Temperatures at or above about 85° C. are usually sufficient to inactivate the proteolytic enzyme, such as the preferred alkaline proteolytic enzyme.

Beyond the objective of inactivating the proteolytic enzyme, the heating step and the manner in which the heating step is performed are not believed to be critical to achieving the benefits of the present invention. Furthermore, the heating step may be achieved by heating the slurried vegetable protein product in the batch reactor or by circulating the slurried vegetable protein product through a heat exchanger, a jet cooker, or any similar heating device of the type typically employed for heating food products in the food manufacturing industry.

Following inactivation of the proteolytic enzyme, such as the preferred alkaline proteolytic enzyme, the slurried vegetable protein product may be comminuted to ensure that any fibrous material is broken apart prior to drying the slurried vegetable protein product. Alternatively, the comminution may be carried out prior to inactivating the proteolytic enzyme. In any event, comminution ensures uniformity of the slurried vegetable protein product and helps to ensure that uniform drying occurs. One example of suitable equipment for achieving adequate comminution is the COMITROL® Model No. 1700 processor that is available from Urschel Laboratories, Inc of Valparaiso, Ind.

Following proteolytic enzyme inactivation and any comminution, the slurried vegetable protein product is dried. The slurried vegetable protein product may be dried using any drying technique or equipment, such as a drum dryer, a vibrating bed dryer, or any type of flash dryer. However, the slurried vegetable protein product is preferably flash dried because flash drying creates a uniform powdered product. Spray drying is the most commonly used flash drying technique, though freeze drying may also be employed. Some examples of suitable spray dryers include vertical spray dryers (VRS dryers) and horizontal spray dryers (HRS dryers) that are available from C. E. Rogers Co. of Northville, Mich., and tower spray dryers that are available from Niro Inc. of Columbia, Md. The slurried vegetable protein product may optionally be cooled, such as to a temperature of about 65° C., prior to drying. The drying step transforms the slurried vegetable protein product into powdered vegetable protein product.

The enzymatic hydrolysis that is accomplished in accordance with the present invention yields a number of different benefits. For example, the enzymatic hydrolysis dramatically decreases the concentration of both glycinin and β-conglycinin, the predominant antigenic proteins, in the powdered vegetable protein product as compared to the concentration of these antigenic proteins in the vegetable protein material that is used to form the slurried vegetable protein feed. This reduction of antigenic protein content in the powdered vegetable protein product greatly reduces the likelihood that use of the powdered vegetable protein product in animal feed and human food would lead to the development of allergies and/or difficulties digesting the powdered vegetable protein product.

As used herein, unless otherwise indicated, the concentration of glycinin in the vegetable protein material is expressed in terms of the weight of glycinin in the vegetable protein material relative to the weight of crude protein in the vegetable protein material, the concentration of glycinin in the slurried vegetable protein product is expressed in terms of the weight of glycinin in the slurried vegetable protein product relative to the weight of crude protein in the slurried vegetable protein product, and the concentration of glycinin in the powdered vegetable protein product is expressed in terms of the weight of glycinin in the powdered vegetable protein product relative to the weight of crude protein in the powdered vegetable protein product. Also, as used herein, unless otherwise indicated, the concentration of β-conglycinin in the vegetable protein material is expressed in terms of the weight of β-conglycinin in the vegetable protein material, the concentration of β-conglycinin in the slurried vegetable protein product is expressed in terms of the weight of β-conglycinin in the slurried vegetable protein product relative to the weight of crude protein in the slurried vegetable protein product, and the concentration of β-conglycinin in the powdered vegetable protein product is expressed in terms of the weight of β-conglycinin in the powdered vegetable protein product relative to the weight of crude protein in the powdered vegetable protein product.

The particular proteolytic enzyme(s) employed in the enzymatic hydrolysis of the present invention, such as the preferred alkaline proteolytic enzyme(s), in combination with the conditions present during the enzymatic hydrolysis and the enzyme deactivation step of the present invention, should be effective (1) to reduce the concentration of glycinin by at least about 50 percent, more preferably by at least about 70 percent, and most preferably by at least about 85 percent, in the powdered vegetable protein product as compared to the vegetable protein material and (2) to reduce the concentration of β-conglycinin by at least 99 percent, more preferably by about 100 percent, and most preferably by 100 percent, in the powdered vegetable protein product as compared to the concentration of β-conglycinin in the vegetable protein material. Furthermore, the particular proteolytic enzyme(s), such as the preferred alkaline proteolytic enzyme(s), and the conditions employed during the enzymatic hydrolysis and the enzyme deactivation step should be effective to reduce the combined concentration of glycinin and β-conglycinin by at least about 70 percent, more preferably by at least about 80 percent, and most preferably by at least about 92 percent in the powdered vegetable protein product, as compared to the combined concentration of glycinin and β-conglycinin in the vegetable protein material.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units and (2) the period of enzymatic hydrolysis is about 5 minutes to about 120 minutes, preferably about 5 to about 90 minutes, and more preferably about 5 to about 60 minutes, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, is preferably effective (a) to reduce the concentration of glycinin by at least about 50 percent, more preferably by at least about 70 percent, and most preferably by at least about 85 percent, in the powdered vegetable protein product as compared to the vegetable protein material and/or (b) to reduce the concentration of β-conglycinin by at least 99 percent, more preferably by about 100 percent, and most preferably by 100 percent, in the powdered vegetable protein product as compared to the concentration of β-conglycinin in the vegetable protein material.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units and (2) the period of enzymatic hydrolysis is about 5 minutes to about 120 minutes, preferably about 5 to about 90 minutes, and more preferably about 5 to about 60 minutes, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, is preferably effective to reduce the combined concentration of glycinin and β-conglycinin by at least about 70 percent, more preferably by at least about 80 percent, and most preferably by at least about 92 percent in the powdered vegetable protein product, as compared to the combined concentration of glycinin and β-conglycinin in the vegetable protein material.

Another benefit of the process of the present invention is the enhanced solubility of the powdered vegetable protein product in water, as compared to the solubility of the vegetable protein material in water. Besides reducing the antigenicity of the powdered vegetable protein product, the process of the present invention additionally enhances the water solubility of proteins present in the powdered vegetable protein product, as compared to the water solubility of the proteins present in the vegetable protein material. The solubility of protein in a particular sample may be characterized based upon the Protein Dispersion Index (PDI) of the sample.

When the vegetable protein material has a PDI of about 60 percent, or more, the process of the present invention is effective to increase the PDI of the powdered vegetable protein product, as compared to the PDI of the vegetable protein material, by at least about 20 percent (for example, changing from a starting PDI of about 62 percent to a PDI of at least about 82 percent), more preferably by at least about 23 percent (for example, changing from a starting PDI of about 62 percent to a PDI of at least about 85 percent), and most preferably by at least about 26 percent (for example, changing from a starting PDI of about 62 percent to a PDI of at least about 88 percent). When the PDI of the vegetable protein material is less than about 60 percent, the process of the present invention is effective to increase the PDI of the powdered vegetable protein product that is based upon the vegetable protein material to greater than about 60 percent, is preferably effective to increase the PDI of the powdered vegetable protein product to at least about 70 percent, and is more preferably effective to increase the PDI of the powdered vegetable protein product to at least about 80 percent.

Preferably, when the PDI of the vegetable protein material is about 40 percent, or less, the process of the present invention is effective to increase the PDI of the powdered vegetable protein product that is based upon the vegetable protein material to greater than about 60 percent, is more preferably effective to increase the PDI of the powdered vegetable protein product to at least about 70 percent, and is still more preferably effective to increase the PDI of the powdered vegetable protein product to at least about 80 percent. More preferably, when the PDI of the vegetable protein material is about 20 percent, or less, the process of the present invention is effective to increase the PDI of the powdered vegetable protein product that is based upon the vegetable protein material to greater than about 60 percent, is still more preferably effective to increase the PDI of the powdered vegetable protein product to at least about 70 percent, and is even more preferably effective to increase the PDI of the powdered vegetable protein product to at least about 80 percent.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units, (2) the period of enzymatic hydrolysis is about 5 minutes to about 120 minutes, preferably about 5 to about 90 minutes, and more preferably about 5 to about 60 minutes, and (3) the vegetable protein material has a PDI of about 60 percent, or more, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, are preferably effective to increase the PDI of the powdered vegetable protein product, as compared to the PDI of the vegetable protein material, by at least about 20 percent, more preferably by at least about 23 percent, and most preferably by at least about 26 percent.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units, (2) the period of enzymatic hydrolysis is about 5 minutes to about 120 minutes, preferably about 5 to about 90 minutes, and more preferably about 5 to about 60 minutes, and the vegetable protein material has a PDI of less than about 60 percent, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, are preferably effective to increase the PDI of the powdered vegetable protein product that is based upon the vegetable protein material to greater than about 60 percent, more preferably to at least about 70 percent, and still more preferably to at least about 80 percent.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units, (2) the period of enzymatic hydrolysis is about 5 minutes to about 120 minutes, preferably about 5 to about 90 minutes, and more preferably about 5 to about 60 minutes, and the vegetable protein material has a PDI of about 40 percent, or less, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, are preferably effective to increase the PDI of the powdered vegetable protein product that is based upon the vegetable protein material to greater than about 60 percent, more preferably to at least about 70 percent, and still more preferably to at least about 80 percent.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units, (2) the period of enzymatic hydrolysis is about 5 minutes to about 120 minutes, preferably about 5 to about 90 minutes, and more preferably about 5 to about 60 minutes, and the vegetable protein material has a PDI of about 20 percent, or less, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, are preferably effective to increase the PDI of the powdered vegetable protein product that is based upon the vegetable protein material to greater than about 60 percent, more preferably to at least about 70 percent, and still more preferably to at least about 80 percent.

The enhanced solubility of the powdered vegetable protein product in water, as compared to the solubility of the vegetable protein material in water, is believed to be due in significant part to the protein (or peptide) molecular weight reduction that is achieved in the powdered vegetable protein product, as compared to the protein molecular weight of the vegetable protein material. In this regard, when the vegetable protein material has an average protein molecular weight in the range of about 125 kilodaltons to about 440 kilodaltons, the process of the present invention is preferably effective to produce the powdered vegetable protein product with an average protein molecular weight of about 7500 Daltons or less, more preferably about 5000 Daltons or less, still more preferably about 2500 Daltons or less, even more preferably about 2000 Daltons or less, yet more preferably about 1500 Daltons or less, and most preferably about 1250 Daltons or less. As used herein, the term "average protein molecular weight" means the average molecular weight of both proteins and protein fragments (peptides) in the sample being considered.

When (1) the slurried vegetable feed has a pH of at least about 7.0 standard pH units, preferably at least about 8.5 standard pH units, more preferably above about 8.5 standard pH units to about 9.5 standard pH units, and even more preferably from about 9.0 standard pH units to about 9.5 standard pH units, (2) the period of enzymatic hydrolysis is about 5 minutes to about 120 minutes, preferably about 5 to about 90 minutes, and more preferably about 5 to about 60 minutes, and (3) the vegetable protein material has an average protein molecular weight in the range of about 125 kilodaltons to about 440 kilodaltons, the particular proteolytic enzyme employed in the enzymatic hydrolysis of the present invention, in combination with the conditions present during the enzymatic hydrolysis period (including, but not limited to, the pH conditions and time of enzymatic hydrolysis that are referred to in (1) and (2) above) and the enzyme deactivation step of the present invention, are preferably effective to produce the powdered vegetable protein product with an average protein molecular weight of about 7500 Daltons or less, more preferably about 5000 Daltons or less, still more preferably about 2500 Daltons or less, even more preferably about 2000 Daltons or less, yet more preferably about 1500 Daltons or less, and most preferably about 1250 Daltons or less.

Furthermore, beyond reducing antigenicity levels in the powdered vegetable protein product and increasing protein solubility in the powdered vegetable protein product, as compared to antigenicity levels and protein solubility in the vegetable protein material, the process of the present invention additionally tends to reduce off-flavors in the powdered vegetable protein product, as compared to off-flavors present in the vegetable protein material.

Thus, three major beneficial aspects of the process of the present invention include reducing antigenicity levels in the powdered vegetable protein product, increasing protein solubility in the powdered vegetable protein product, and reducing off-flavors in the powdered vegetable protein product, as compared to the levels of these variables in the vegetable protein material. Consequently, after drying, the powdered vegetable protein product may be employed in a wide variety of food substrates, destined for consumption by both animals and humans, to increase the nutritional value of the food substrates. For example, the powdered vegetable protein product may be incorporated in milk replacers for feeding monogastric mammals, such as human babies and young animals with only one functioning stomach, such as young calves, while enhancing the solubility and stability of the powdered vegetable protein product in the milk replacer and reducing chances for allergic reaction in the mammals fed the milk replacer. Furthermore, the powdered vegetable protein product may be incorporated in a number of different human foods, such as gelatins, beverages, and other foods that would benefit from a highly soluble source of protein with low propensity for allergic inducement.

Property Determination & Characterization Techniques

Various analytical techniques are employed herein. An explanation of these techniques follows. All values presented in this document for weight percent dry matter for a particular sample are based on the "as is" form of the sample and are therefore on a "wet basis," unless otherwise specified herein. All values presented in this document for certain other parameters in a sample, namely, weight percent organic matter, weight percent ash, and weight percent crude protein, are based on the dry matter weight of the sample and are therefore on a "dry matter" or "dry" basis, unless otherwise specified herein. Furthermore, all values presented in this document for weight percent soluble protein and for concentrations of glycinin and β-conglycinin in a particular sample are based upon the weight of crude protein in the sample, unless otherwise specified herein.

pH Determinations

Unless otherwise indicated, all pH determinations recited or specified herein are based upon use of the Model No. 59003-00 Digital Benchtop pH/mV Meter that is available from Cole-Parmer Instrument Co. of Vernon Hills, Ill. using the procedure set forth in the instructions accompanying the Model No. 59003-00 Digital Benchtop pH/mV Meter. All pH values recited herein were determined at or are based upon a sample temperature of about 25° C.

Dry Matter Weight Determination

The weight percent of dry matter in a particular sample, based upon the total weight of the sample, is calculated after first determining the moisture content in the sample. The weight of moisture in a particular sample is determined by analyzing the sample in accordance with Method #930.15 (4.106) of *Official Methods of Analysis*, Association of Official Analytical Chemists (AOAC) (16$^{th}$ Ed., 1995). The weight percent moisture in the sample, based upon the total weight of the sample, is then calculated by dividing the actual weight of moisture in the sample by the total weight of the sample and then multiplying the result of this division by 100%. The weight percent dry matter in the sample is then determined by subtracting 100% from the weight percent of moisture in the sample. For example, if a particular sample had a moisture concentration of 22 weight percent, then the dry matter content of that sample would be 78 weight percent. The weight percent dry matter in the is also known as the weight percent total solids in the sample.

Ash and Organic Matter Determinations

The weight percent ash, dry basis, in a particular sample is determined after first determining the weight of ash in the sample. The weight of ash in a particular sample is determined by analyzing the sample in accordance with Method #942.05 (4.1.10) of *Official Methods Of Analysis*, Association of Official Analytical Chemist (AOAC) (16$^{th}$ Ed., 1995). The weight percent ash, dry basis, in the sample is then calculated by dividing the actual weight of ash by the weight of dry matter in the sample, that is determined by Method #930.15 as described above, and then multiplying this result of this division by 100%. The weight percent organic matter, dry basis, in the sample is then calculated by subtracting the weight percent ash, dry basis, in the sample from 100%. Thus, if the weight percent ash, dry basis, in a particular sample is 30 weight percent, the weight percent organic matter, dry basis, in the sample is consequently 70 weight percent.

Crude Protein Determination

The weight percent crude protein, dry basis, in a particular sample is calculated after first determining the actual weight of total protein in the sample. The actual weight of total protein in the sample is determined in accordance with Method #991.20 (33.2.11) of *Official Methods of Analysis*, Association of Official Analytical Chemists (AOAC) (16$^{th}$ Ed., 1995). The value determined by the above method yields "total Kjeldahl nitrogen," which is equivalent to "total protein," since the above method incorporates a factor that accounts for the average amount of nitrogen in protein. Total Kjeldahl nitrogen and total protein are sometimes referred to in the dairy industry as "crude protein." Consequently, the terms "total Kjeldahl nitrogen," "crude protein," and "total protein" are used interchangeably herein. Furthermore, those skilled in the art will recognize that the term "total Kjeldahl nitrogen" is generally used in the art to mean "crude protein" or "total protein" with the understanding that the above-noted nitrogen factor has been applied.

The weight percent crude protein, dry basis, in the sample is calculated by dividing the actual weight of crude protein (a.k.a. total Kjeldahl nitrogen) by the weight of dry matter in the sample, that is determined by Method #930.15 as described above, and then multiplying this result by 100%. The weight percent crude protein in the sample, based on the organic matter content of the sample, is calculated by dividing the weight percent crude protein, dry basis, of the sample by the weight percent organic matter, dry basis, in the sample, determined as described above in Ash and Organic Matter Determinations, and multiplying the result of this division by 100%.

Protein Dispersability Index (PDI) Determination

This method is used to determine the Protein Dispersability Index (PDI) of a particular sample that contains protein. The Protein Dispersability Index is a measure of the soluble protein content in a sample, expressed as a percent, by weight, of the crude protein weight in the sample. Consequently, the Protein Dispersability Index is equivalent to the weight percent of soluble protein in a sample, based upon the weight of crude protein in the sample. The Protein Dispersability Index (PDI) of a particular sample that contains protein may be determined in accordance with Method No. 46-24 (1995), entitled *Protein Dispersability Index*, of the American Association of Cereal Chemists (AACC). The current address of the American Association of Cereal Chemists is 3340 Pilot Knob Road, St. Paul, Minn. 55121.

Brookfield Viscosity Determination

Unless otherwise indicated, all viscosities recited herein were determined using a Brookfield Model No. DV-II+ viscometer that may be obtained from Brookfield Engineering Laboratories of Middleboro, Mass. Any of spindle nos. 4, 5, and/or 6 that are available from Brookfield Engineering Laboratories for use with the Model No. DV-II+ viscometer may be used when determining the viscosity of a particular sample. Viscosity determinations were conducted in accordance with the Operating Instructions manual for the Brookfield Model No. DV-II+ viscometer, unless otherwise indicated herein. Unless otherwise indicated herein, viscosity measurements were determined with the sample at a particular temperature and, consequently, sample temperatures are provided with each viscosity determination provided herein.

Protein Fragment Size Analysis by HPLC

The molecular weight distribution (or profile) for proteins and peptides in different samples may be determined using High Pressure Liquid Chromatography ("HPLC"). A Waters High Pressure Liquid Chromatography system employing a Waters 510 high pressure pump, a Waters 712 WISP automatic sample injection system, and a Waters 996 Photodiode Array detector may be used. The Waters High Pressure Liquid Chromatography system employing the specified components maybe obtained from Waters Corporation of Milford, Mass.

Some non-exhaustive examples of samples that maybe analyzed by this HPLC method include supernatant samples obtained after centrifuging a solution of the vegetable protein feed or a solution of the powdered vegetable protein product. The solution of the vegetable protein feed or of the powdered vegetable protein product maybe prepared by blending together about 3.2 grams of the vegetable protein feed or of the powdered vegetable protein product with about 40 milliliters of distilled, deionized water to form a slurry. The slurry is placed in a 50 milliliter centrifuge tube and then incubated at 30° C. for about three hours with intermittent mixing. After the three hour incubation period, the 50 milliliter centrifuge tube containing the slurry is placed in a centrifuge. After assuring that the centrifuge is balanced, the centrifuge is operated for 10 minutes at a rate of about 2700 revolutions per minute. Then, the supernatant layer that forms in the 50 milliliter centrifuge tube when centrifuging the slurry is used as the sample in the HPLC procedure.

In the Waters HPLC system, the Waters 996 Photodiode Array detector is set at 206 nanometers. The stationary phase of the chromatographic system is a BioSep SEC-S2000 size exclusion column that may be obtained from PHENOMENEX INC. of Torrance, Calif. The mobile phase of the chromatographic system is a solution of 100 mM sodium phosphate with a pH of 6.8. The sample flow rate in the system is set at 1.0 ml/minute for samples of the vegetable protein feed, and the sample flow rate in the system is set at 1.0 ml/minute for samples of the powdered vegetable protein product. The data obtained from the HPLC analysis is printed as a graph showing molecular weight distribution (profile) of protein fragments, expressed in absorption units, as a function of retention time. The molecular weights of proteins and peptides in a sample, expressed in Daltons, maybe determined from a standard curve for proteins and peptides of known molecular weight analyzed by the above-described HPLC procedure to produce a molecular weight profile for the sample. The distribution of protein molecular weights for the proteins and peptides in the sample may be averaged to determine the average protein molecular weight of the sample.

Glycinin and β-conglycinin Determinations

The determination of Glycinin content and β-Conglycinin content in a particular sample may be conducted in accordance with the following procedure, which is based upon an Enzyme-Linked Immunosorbent Assay (subsequently referred to as "ELISA"). The procedure is conducted in four separate steps: Isolation of Native Glycinin and β-Conglycinin, Antibody Preparation, ELISA Assay, and Calculations.

Isolation of Native Glycinin and β-Conglycinin

Native Glycinin and β-Conglycinin are isolated from a raw defatted soybean flour composition by placing about three grams of the raw (i.e.: not denatured or enzymatically-degraded) defatted soybean flour composition into fifteen milliliters (ml) of a 0.15 molar (M) sodium chloride (NaCl) solution. The mixture of the flour composition and the NaCl solution are held for about 1 hour at 25° C., while maintaining the pH of the mixture at 6.7 with a 1.0 M sodium hydroxide (NaOH) solution, to form a native Glycinin and β-Conglycinin extract. The NaCl and NaOH reagents are available from Sigma Chemical Company of Saint-Quentin Fallavier, France.

Next, the native Glycinin and β-Conglycinin extract is clarified by centrifugation at 1,100×g for 30 minutes at 20° C. A supernatant of the Glycinin and P-Conglycinin extract obtained after centrifugation is then further purified using gel filtration. About 0.5 ml of the supernatant is applied to a Sephacryl L S300-HR column previously equilibrated with a PBS buffer. The supernatant is separated into 1-ml fractions using a PBS buffer elution rate of about 100 ml per hour. The PBS buffer should contain 0.2 grams of potassium chloride (KCl) per liter, 0.2 grams of potassium di-hydrogen phosphate ($KH_2PO_4$) per liter, 8.0 grams of sodium chloride (NaCl) per liter, 1.14 grams of di-sodium hydrogen phosphate ($Na_2HPO_4$) per liter, and 0.1 grams of Kathon per liter.

The Sephacryl L S300-HR column is available from Pharmacia of Saint Quentin-en-Yvelines, France, while the various PBS reagents are available from Sigma Chemical Company of Saint-Quentin Fallavier, France. Individual purified native Glycinin and β-Conglycinin fractions are recovered by gel filtration as single peaks at elution volumes that corresponded to molecular weights (MW) of 340-440 kiloDaltons (kD) for Glycinin, and 180-230 kD for β-Conglycinin. The purified native Glycinin fraction and the purified native β-Conglycinin fraction are stored at −20° C. until required.

The purity of the native Glycinin fraction and the purity of the native β-Conglycinin fraction are confirmed using sodium dodecyl sulphate-polyacrylamide gel electrophoresis (SDS-PAGE). Mini-gels (80 millimeters (mm)×90 mm) include a 12.5 weight percent acrylamide separating gel and a 4 weight percent acrylamide stacking gel. Protein loadings are 5 microgram (μg) of protein per track for the native Glycinin fraction and also for the native β-Conglycinin fraction. SDS-PAGE is performed in the presence of a Laemmli buffer system that includes Tris-glycine containing 25 millimolar (mM) Tris, 192 mM glycine and, 2 grams of SDS per liter, at a pH of 8.3 under reducing conditions of about 2 weight percent mercaptoethanol. Molecular weight standards are also loaded in a separate well. Electrophoresis is performed for 1.5 hours at 40 mA. Gels are stained for protein using 0.25 percent Coomassie brilliant blue R250 in methanol:acetic acid:water (5:1:4 vol/vol/vol). The SDS-PAGE reagents described above are available from Sigma Chemical Company of La Verpilliere, France.

Antibody Preparation

Antisera are produced in New Zealand White Rabbits that were supplied by Ranch Rabbits Ltd of Capthorn, Sussex. The antisera are produced against the purified native Glycinin and β-Conglycinin obtained in accordance with the method described above in the section of this document entitled "Isolation of Glycinin and β-Conglycinin."

Antisera for Glycinin are produced by emulsifying one (1) milligram (mg) of the purified native Glycinin in 1.0 ml of Freund's complete adjuvant. About 0.7 ml of this Glycinin-based emulsion is administered intramuscularly to the rabbits on two or three occasions over a five to seven week period. Antisera for β-Conglycinin are produced by emulsifying one (1) milligram (mg) of the purified native β-Conglycinin in 1.0 ml of Freund's complete adjuvant. About 0.7 ml of this β-Conglycinin-based emulsion is administered intramuscularly to the rabbits on two or three occasions over a five to seven week period.

ELISA Assay

Unless otherwise indicated, all reagents used to perform the ELISA Assay may be obtained from Sigma Chemical Corporation of Saint-Quentin Fallavier, France.

1. Sample Extraction

Soybean proteins are extracted for about 1.5 hours from a sample (also referred to herein as the "test protein sample") of the soybean protein composition under consideration using 100 volumes of a borate buffer solution at room temperature of about 22° C. The borate buffer solution has a pH of about 8.0 units and contains 100 mM Sodium Perborate ($Na_2BO_3$) and 0.15 M NaCl. The soybean protein extract obtained from the test protein sample (also referred to herein as the "test protein sample extract") is clarified by centrifugation at 20,000×g for 15 minutes.

2. Glycinin Determination by ELISA Assay a. Initial Plate Preparation

Two NUNC Immunoplate I microtitration plates, obtained from Gibco Europe, Paisley, United Kingdom, are coated with a solution containing purified native Glycinin obtained in accordance with the method described above in the section of this document entitled "Isolation of Glycinin and β-Conglycinin." One of the coated plates is used for determining the Glycinin content of the test protein sample and one of the coated plates is used for determining the Glycinin content of the protein standards samples.

Prior to coating the two plates, the purified native Glycinin is dissolved in a buffer of 50 mM sodium carbonate buffer at a pH of 9.6 to form a buffered solution containing 1 μg of purified native Glycinin per ml of the buffered solution. The two plates are then coated with the purified native Glycinin by adding 0.3 ml of the buffered solution in each well of the plates. The two coated plates are then incubated for 16 hours at 4° C. After incubation, the two coated plates are washed three times with a solution of TWEEN® surfactant and sodium chloride. After washing, the coated and incubated plates are blotted and stored at −20° C. for no longer than 4 weeks.

b. Test Protein Sample

One of the coated and incubated plates prepared in subsection a. above entitled "Initial Plate Preparation" is employed in the ELISA assay of the Test Protein Sample. The Glycinin antisera obtained in accordance with the method described above (see section above entitled "Antibody Preparation") is diluted to a ratio of about 1:32,000 (v/v) with PBS. Equal volumes of the test protein sample extract (see section 1. above entitled "Sample Extraction") and the diluted antisera are combined to form a mixture. Two hundred (200) μl of the mixture are added to each well of the coated plate. The coated plate is then incubated at 37° C. for 4 hours. After incubation, the plate is washed three times with an aqueous solution of NaCl and TWEEN® surfactant.

After washing, 0.2 ml of anti-rabbit IgG-horseradish peroxidase conjugate in PBS that has been diluted to 1:2000 (v/v) is added to each well of the coated plate. After adding the diluted anti-rabbit IgG-horseradish peroxidase conjugate, the plate is incubated for 2 hours at 37° C. After incubation, the plate is washed three times with an aqueous solution of NaCl and TWEEN® surfactant.

After washing, aqueous solutions of 2,2'-azinobis(3-ethylbenzthiazoline-6-sulfonic acid) and hydrogen peroxide, each at a concentration of 0.01 weight percent, are added to the coated plate, and the coated plate is incubated for 30 minutes at room temperature. The optical density of the plate at the various wells of the plate is then read at a detection wavelength of 405 nanometers for 10 seconds using an Argus 300 plate reader from Packard Instruments Company of Meriden, Conn.

c. Protein Standards Samples

One of the coated and incubated plates prepared in subsection a. above entitled "Initial Plate Preparation" is employed in the ELISA assay of the protein standards samples. The Glycinin antisera obtained in accordance with the method described above (see section above entitled "Antibody Preparation") is diluted to a ratio of about 1:32,000 (v/v) with PBS.

A standard solution of Glycinin in PBS at a concentration of 2 mg of Glycinin per ml of the standard solution is diluted to give a range of different glycinin standards ranging from 100 nanograms (ng) of glycinin per ml to 1 mg of Glycinin per ml. The number of different glycinin standards may, as an example, be equal to the number of wells that are included in the plate.

For each of the individual glycinin standards, equal volumes of the particular glycinin standard and the diluted antisera are combined to form a glycinin standard/antisera mixture. Therefore, the number of glycinin standard/antisera mixtures is equal to the number of different glycinin standards. Two hundred (200) μl of each glycinin standard/antisera mixture are added to different wells of the coated plate. Therefore, as an example, each well of the coated plate may contain a different one of the glycinin standard/antisera mixtures, if the number of different glycinin standards equals the number of wells in the plate. The coated plate is then incubated at 37° C. for 4 hours. After incubation, the plate is washed three times with an aqueous solution of NaCl and TWEEN® surfactant.

After washing, 0.2 ml of anti-rabbit IgG-horseradish peroxidase conjugate in PBS that has bee diluted to 1:2000 (v/v) is added to each well of the coated plate. After adding the diluted anti-rabbit IgG-horseradish peroxidase conjugate, the plate is incubated for 2 hours at 37° C. After incubation, the plate is washed three times with an aqueous solution of NaCl and TWEEN® surfactant.

After washing, aqueous solutions of 2,2'-azinobis(3-ethylbenzthiazoline-6-sulfonic acid) and hydrogen peroxide, each at a concentration of 0.01 weight percent, are added to the coated plate, and the coated plate is incubated for 30 minutes at room temperature. The optical density of the plate is then read at a detection wavelength of 405 nanometers for 10 seconds using an Argus 300 plate reader from Packard Instruments Company of Meriden, Conn.

3. β-Conglycinin Determination by ELISA Assay a. Initial Plate Preparation

Two NUNC Immunoplate I microtitration plates, obtained from Gibco Europe, Paisley, United Kingdom, are coated with a solution containing purified native β-Conglycinin obtained in accordance with the method described above in the section of this document entitled "Isolation of Glycinin and β-Conglycinin." One of the coated plates is used for determining the β-Conglycinin content of the test protein sample and one of the coated plates is used for determining the β-Conglycinin content of the protein standards samples.

Prior to coating the two plates, the purified native β-Conglycinin is dissolved in a buffer of 50 mM sodium carbonate buffer at a pH of 9.6 to form a buffered solution containing 1 µg of purified native β-Conglycinin per ml of the buffered solution. The two plates are then coated with the purified native β-Conglycinin by adding 0.3 ml of the buffered solution in each well of the plates. The two coated plates are then incubated for 16 hours at 4° C. After incubation, the two coated plates are washed three times with a solution of TWEEN® surfactant and sodium chloride. After washing, the coated and incubated plates are blotted and stored at −20° C. for no longer than 4 weeks.

b. Test Protein Sample

One of the coated and incubated plates prepared in subsection a. above entitled "Initial Plate Preparation" is employed in the ELISA assay of the Test Protein Sample. The β-Conglycinin antisera obtained in accordance with the method described above (see section above entitled "Antibody Preparation") is diluted to a ratio of about 1:16,000 (v/v) with PBS. Equal volumes of the test protein sample extract (see section 1. above entitled "Sample Extraction") and the diluted antisera are combined to form a mixture. Two hundred (200) µl of the mixture are added to each well of the coated plate. The coated plate is then incubated at 37° C. for 4 hours. After incubation, the plate is washed three times with an aqueous solution of NaCl and TWEEN® surfactant.

After washing, 0.2 ml of anti-rabbit IgG-horseradish peroxidase conjugate in PBS that has been diluted to 1:2000 (v/v) is added to each well of the coated plate. After adding the diluted anti-rabbit IgG-horseradish peroxidase conjugate, the plate is incubated for 2 hours at 37° C. After incubation, the plate is washed three times with an aqueous solution of NaCl and TWEEN® surfactant.

After washing, aqueous solutions of 2,2'-azinobis(3-ethylbenzthiazoline-6-sulfonic acid) and hydrogen peroxide, each at a concentration of 0.01 weight percent, are added to the coated plate, and the coated plate is incubated for 30 minutes at room temperature. The optical density of the plate at the various wells of the plate is then read at a detection wavelength of 405 nanometers for 10 seconds using an Argus 300 plate reader from Packard Instruments Company of Meriden, Conn.

c. Protein Standards Samples

One of the coated and incubated plates prepared in subsection a. above entitled "Initial Plate Preparation" is employed in the ELISA assay of the protein standards samples. The β-Conglycinin antisera obtained in accordance with the method described above (see section above entitled "Antibody Preparation") is diluted to a ratio of about 1:16, 000 (v/v) with PBS.

A standard solution of β-Conglycinin in PBS at a concentration of 2 mg of β-Conglycinin per ml of the standard solution is diluted to give a range of different β-Conglycinin standards ranging from 10 nanograms (ng) of β-Conglycinin per ml to 100 µg of β-Conglycinin per ml. The number of different β-Conglycinin standards may, as an example, be equal to the number of wells that are included in the plate.

For each of the individual β-Conglycinin standards, equal volumes of the particular β-Conglycinin standard and the diluted antisera are combined to form a β-Conglycinin standard/antisera mixture. Therefore, the number of β-Conglycinin standard/antisera mixtures is equal to the number of different β-Conglycinin standards. Two hundred (200) µl of each β-Conglycinin standard/antisera mixture are added to different wells of the coated plate. Therefore, as an example, each well of the coated plate may contain a different one of the β-Conglycinin standard/antisera mixtures, if the number of different β-Conglycinin standards equals the number of wells in the plate. The coated plate is then incubated at 37° C. for 4 hours. After incubation, the plate is washed three times with an aqueous solution of NaCl and TWEEN® surfactant.

After washing, 0.2 ml of anti-rabbit IgG-horseradish peroxidase conjugate in PBS that has bee diluted to 1:2000 (v/v) is added to each well of the coated plate. After adding the diluted anti-rabbit IgG-horseradish peroxidase conjugate, the plate is incubated for 2 hours at 37° C. After incubation, the plate is washed three times with an aqueous solution of NaCl and TWEEN® surfactant.

After washing, aqueous solutions of 2,2'-azinobis(3-ethylbenzthiazoline-6-sulfonic acid) and hydrogen peroxide, each at a concentration of 0.01 weight percent, are added to the coated plate, and the coated plate is incubated for 30 minutes at room temperature. The optical density of the plate is then read at a detection wavelength of 405 nanometers for 10 seconds using an Argus 300 plate reader from Packard Instruments Company of Meriden, Conn.

Calculations

A standard curve for glycinin content was prepared based upon the ELISA analysis of the Glycinin protein standards samples. The axes of the standard curve included the known glycinin content of the various Glycinin protein standards samples that were prepared and the optical densities measured when using the various Glycinin protein standards samples. This standard curve for glycinin content was developed using linear regression after logit-log transformation. In the standard curve, the glycinin contents of the various glycinin protein standards samples are stated relative to the crude protein content of the various glycinin protein standards samples, where crude protein contents are determined using the methods of Kjedahl (Crude Protein (CP)=[N]× 6.25). The concentration of glycinin (relative to crude protein content) in test protein sample(s) are obtained from the standard curve for glycinin content, based upon the optical densities measured for the test protein sample(s) when analyzing for glycinin.

Similarly, a standard curve for β-Conglycinin content was prepared based upon the ELISA analysis of the β-Conglycinin protein standards samples. The axes of the standard curve included the known β-Conglycinin content of the various β-Conglycinin protein standards samples that were prepared and the optical densities measured when using the various β-Conglycinin protein standards samples. This standard curve for β-Conglycinin content was developed using linear regression after logit-log transformation. In the standard curve, the β-Conglycinin contents of the various β-Conglycinin protein standards samples are stated relative to the crude protein content of the various β-Conglycinin protein standards samples, where crude protein contents are determined using the methods of Kjedahl (Crude Protein (CP)=[N]×6.25). The concentration of β-Conglycinin (relative to crude protein content) in test protein sample(s) are obtained from the standard curve for β-Conglycinin content, based upon the optical densities measured for the test protein sample(s) when analyzing for β-Conglycinin.

Additional Background Information About the ELISA Procedure

Additional background information about determination of Glycinin content and β-Conglycinin content in a particular sample in accordance with the Enzyme-Linked Immunosorbent Assay ("ELISA") procedure that is provided herein may be obtained from the following publications, which are each hereby incorporated by reference herein, in their entirety:

1. Lallès, J. P., Plumb, G. W., Mills, E. N. C., Morgan, M. R. A, Tukur, H. M., and Toullec, R., *Antigenic Activity of Some Soyabean Products Used in Veal Calf Feeding: Comparison Between In Vitro Tests (ELISA Polyclonal vs Monoclonal) And With In Vivo Data*, Pages 281-285 in van der Poel, A. F. B., Huisman, J., and Saini, H. S., ed., *Recent Advances of Research in AntiNutritional Factors in Legume Seeds*, Publ. No. 70 (1993 Wageningen Pers, Wageningen, The Netherlands);

2. Lallès, J. P., Tukur, H. M., Dréau, D. and Toullec, R., *Contribution of INRA to the Study of Antigenicity of Plant Protein Used in Young Farm Animal Nutrition.* In: Van Oort, M. G. and Tolman, G. H.: *Antigenicity of Legume Proteins*. TNO Communications. 25 pp (1992);

3. Tukur, H. M., Lallès, J. P., Mathis, C., Caugant, I., and Toullec, R., *Digestion of Soybean Globulins, Glycinin, α-conglycinin and β-conglycinin, in the Preruminant and the Ruminant Calf*, Can. J. Anim. Sci., vol. 73, pp. 891-905 (December 1993);

4. Lallès, J. P., Tukur, H. M., Toullec, R., and Miller, B. G., *Analytical Criteria for Predicting Apparent Digestibility of Soybean Protein in Preruminant Calves*, J. Dairy Sci., vol 79, pp 475-482 (1996);

5. Tukur, H. M.; Lallès, J. P.; Plumb, G. W.; Mills, E. N. C.; Morgan, M. R. A.; and Toullec, R., *Investigation of the Relationship Between in Vitro Elisa Measures of Immunoreactive Soy Globulins and in Vivo Effects of Soy Products*, Journal of Agricultural and Food Chemistry, 44 (8) pp. 2155-2161 (1996);

6. Lalles, J. P., Tukur, H. M., Salgado, P., Mills, E. N. C., Morgan, M. R. A., Quillien, L., Levieux, D., and Toullec, R., *Immunochemical Studies on Gastric and Intestinal Digestion of Soybean Glycinin and Beta-conglycinin in Vivo*, Journal of Agricultural and Food Chemistry, 47 (7) pp. 2797-2806 (July, 1999);

7. Lalles, J. P.; Tukur, H. M.; and Toullec, R., *Immunochemical Tests for Measuring Glycinin and Beta-conglycinin Concentrations in Soyabean Products. Predictive Value for Nitrogen Digestibility and Soyabean Immunogenicity in the Calf*, Annales de Zootechnie (Paris), 46 (3), pp 193-205 (1997), CAB Accession Number: 981400459, BIOSIS NO.: 199799684390;

8. Lalles J. P.; Tukur H. M.; and Toullec, R., *Immunochemical Tests for the Determination of Glycinin and Beta-conglycinin Levels in Soya Products for Calf Milk Replacers*, EAAP Publication, vol. 81, pp. 243-244 (1996), BIOSIS NO.: 199699169689;

9. Tukur, H. M., Pardal, P. B., Formal, M., Toullec, R., Lalles, J. P., and Guilloteau, P. *Digestibility, Blood Levels of Nutrients and Skin Responses of Calves Fed Soyabean and Lupin Proteins*, Reproduction Nutrition Development vol. 35 (1) pp. 27-44 (1995);

10. Toullec, R.; Lalles, J. P.; and Tukur, H. M., *Biochemical Characteristics and Apparent Digestibility of Nitrogen in Soyabeans in Pre-ruminant Calves* (Original Title: Caracteristiques Biochimiques et Digestibilite Apparente Des Matieres Azotees De Soja Chez Le Veau Preruminant), ISBN: 2-84148-004-6, pp.229-232, (1994 Institut de l'Elevage, Paris, France);

11. Lalles, J. P., Tukur, H. M., and Toullec, R., *Assessment of the Antigenicity of Soya Products for Calf Milk Replacers: Which Immunochemical Tests to Use?* (*Evaluation De L'antigenicite Des Produits du Soja Destines Aux Aliments D'allaitement Pour Veaux: Quels Tests Immunochimiques Utiliser?*), p. 135 in Proceedings of the 2nd meeting "Rencontres Autour Des Recherches Sur Les Ruminants" of the Institut National de la Recherche Agronomique, held in Paris (France), on Dec. 13 and 14, 1995, (December, 1995, Institut de L'Elevage, Paris, France), ISBN: 2-84148-016-X;

12. Toullec, R., Lalles, J. P., and Tukur, H. M., *Relationships Between Some Characteristics of Soybean Products and Nitrogen Apparent Digestibility in Preruminant Calves* (*Caracteristiques Biochimiques et Digestibilite Apparente Des Matieres Azotees De Soja Chez Le Veau Preruminant*), pp. 229-232 of the Proceedings of the first meeting "Rencontres autour des recherches sur les ruminants". of the Institut National de la Recherche Agronomique, held in Paris (France), on Dec. 1 and 2, 1994, (December, 1994, Institut de l'Elevage, Paris, France), ISBN: 2-84148-004-6;

13. Lalles, J. P. and Toullec, R., *Soybean Products in Milk Replacers for Farm Animals: Processing, Digestion and Adverse Reactions*, CAB Accession Number: 991411987;

14. Lalles, J. P., Heppell, L. M. J., Sissons, J. W., and Toullec, R., *Antigenicity of Dietary Protein from Soyabean Meal and Peas in the Dairy Calf Throughout Weaning*, CAB Accession Number: 920451145;

15. Dreau, D., Larre, C., and Lalles, J. P. *Semi-quantitative Purification and Assessment of Purity of Three Soybean Proteins—Glycinin, Beta-conglycinin and Alpha-conglycinin—by Sds-page Electrophoresis, Densitometry and Immunoblotting*, Journal of Food Science and Technology, India, vol. 31 (6), pp. 489-493 (1994), ISSN: 0022-1155;

16. Heppell, L. M. J., Sissons, J. W., and Pedersen, H. E., *A Comparison of the Antigenicity of Soybean-based Infant Formulas*, British Journal of Nutrition, vol. 58 (3), pp.393-404 (1987);

17. Sissons, J. W. and Thurston, S. M., *Survival of Dietary Antigens in the Digestive Tract of Calves Intolerant to Soyabean Products*, Research in Veterinary Science vol. 37 (2): pp. 242-246 (1984);
18. Sissons, J. W., Nyrup, A., Kilshaw, P. J.; and Smith, R. H., *Ethanol Denaturation of Soybean Protein Antigens*, Journal of the Science of Food and Agriculture, vol. 33 (8): pp. 706-710 (1982);
19. Kilshaw, P. J., and Sissons, J. W., *Gastrointestinal Allergy to Soyabean Protein in Preruminant Calves. Allergenic Constituents of Soyabean Products*, Research in Veterinary Science, vol. 27 (3): pp. 366-371 (1979);
20. Heppel, L. M. J., *Determination of milk protein Denaturation by an Enzyme-Linked Immunosorbent Assay*, Pages 115-123 in Morris, B. A. and Clifford, M. N., eds., *Immunoassays in Food Analysis* (1985 Elsevier Applied Science publishers, London, England); and
21. Bush, R. S., Toellec, R., Caugant, I., and Guilloteau, P., *Effects of Raw Pea Flour on Nutrient Digestibility and Immune Responses in the Preruminant Calf*, J. Dairy Sci., vol. 75, pp. 3539-3552 (1992).
22. Perez, M. D., Mills, E N Clare, Lambert, N., Johnson, I. T., and Morgan, M. R. A., *The Use of Anti-Soya Globulin Antsera in Investigating Soya Digestion In Vivo*, J. of the Science of Food and Agriculture, vol. 80, pp. 513-521 (2000).

EXAMPLES

The present invention is more particularly described in the following examples which are intended as illustrations only since numerous modifications and variations within the scope of the present invention will be apparent to those skilled in the art.

Example 1

This example demonstrates the effectiveness of the process of the present invention for substantially enhancing the Protein Dispersability Index (PDI) of soy flakes and for substantially decreasing the content of antigenic proteins, such as glycinin and β-conglycinin, in soy flakes that are treated in accordance with the process of the present invention. In Example 1, 110 gallons (416.4 liters) {968 pounds (439.1 kilograms)} of warm water were added to a 240 gallon (908 liter) tank (subsequently referred to as a "batch reactor"). The batch reactor was equipped with an agitator. The batch reactor was also equipped with a jacket for accommodating steam or hot water circulation to maintain or change the temperature of the contents of the batch reactor. With the water at a temperature of about 50° C., 300 pounds (136.1 kilograms) of soy flakes were added to the warm water in the batch reactor under slow agitation to form a homogenous slurry of the soy flakes and water. The soy flakes were obtained from Harvest States Oilseed Processing & Refining of Mankato, Minn. After addition of the soy flakes was completed, hot water was circulated through the jacket of the batch reactor to raise the temperature of the slurry to about 53° C.

After formation of the slurry of soy flakes and water, the initial pH of the slurry was about 6.35 standard pH units. About 12 liters of a solution of 10 weight percent NaOH, based upon the total weight of the sodium hydroxide solution, was added to the slurry to adjust the pH of the slurry to about 9.00 standard pH units. The amount of sodium hydroxide solution that was added boosted the pH of the slurry higher than desired. Therefore, with the slurry still under agitation, about four liters of an aqueous acid solution containing about 10 weight percent hydrochloric acid, based upon the total weight of the aqueous acid solution, was gradually added to the agitated slurry until the pH of the slurry was reduced to about 8.48 standard pH units.

About 3 pounds (1360 grams) {about 1500 milliliters} of MULTIFECT® P-3000 enzyme composition were then added to the slurry in the batch reactor while agitating the slurry. Thus, the MULTIFECT® P-3000 enzyme composition was added to the slurry at a ratio of about one pound (454 grams) of MULTIFECT® P-3000 enzyme composition per one hundred pounds (45.35 kilograms) of soy flakes. The MULTIFECT® P-3000 enzyme composition, which is a dark amber colored liquid, was obtained from Genencor International, Inc. of Santa Clara, Calif. The addition of the MULTIFECT® P-3000 enzyme composition initiated an enzymatic hydrolysis reaction that was allowed to continue in the batch reactor for a period of about two hours while maintaining the slurry at a temperature ranging from about 53° C. to about 55° C. and while maintaining mild agitation of the slurry.

No caustic or acid was added to the slurry during the enzymatic hydrolysis, and the pH of the slurry was observed to drop to about 7.07 standard pH units after the two-hour period of enzymatic hydrolysis. At the end of the two hour enzymatic hydrolysis period, steam was passed through the jacket of the batch reactor and the slurry was heated to about 85° C. to inactivate the alkaline proteolytic enzyme. Temperature and pH details during the two hour period of enzymatic hydrolysis and temperature details during the heating to inactivate the enzymes are provided below in Table 1:

TABLE 1

| Description | Time (minutes) | pH | Temp (° C.) |
| --- | --- | --- | --- |
| Start of Enzymatic Hydrolysis | 0 | 8.48 | 53.0 |
| | 20 | | 55.3 |
| | 60 | 7.13 | 54.6 |
| | 85 | 7.08 | 54.0 |
| Start of Heating to Inactivate Enzymes | 117 | 7.07 | 53.2 |
| | 123 | | 57.6 |
| | 131 | | 64.4 |
| Target Enzyme Inactivation Temp. Achieved | 150 | | 85.0 |
| Enzyme Inactivation Completed | 155 | | 85.0 |

Heating of the slurry to inactivate the alkaline proteolytic enzyme was begun at time 117 (minutes). The slurry was held at about 85° C. for about 5 minutes.

After enzyme inactivation was completed, the slurry was then pumped from the batch reactor to a pair of 120 gallon (454 liter) storage tanks equipped with agitators. Cold water was circulated through the jacket of the batch reactor during the transfer of the slurry to the storage tanks. Also, en route to the storage tanks, the slurry was passed through a COMITROL® Model No. 1700 processor to ensure that any fibrous material in the slurry was broken apart prior to drying. After transfer of the slurry through the COMITROL® processor and to the storage tanks was completed, 10 gallons (37.8 liters) of hot tap water was added to the slurry in one of the storage tanks and 15 gallons (56.8 liters) of hot tap water was added to the slurry in the other of the storage tank to facilitate subsequent spray drying. After hot water addition was completed, the diluted slurry in each of the storage tanks was introduced into a vertical spray dryer, supplied by C. E. Rogers Co. of Northville, Mich., to produce spray dried soy powder. The recovery rate for the processing described above in this example was about 90.7%, since 300 pounds (136.1 kilograms) of soy flakes were introduced into the batch reactor, and 272 pounds (123.4 kilograms) of spray dried soy powder were recovered from the spray dryer.

Samples of the soy flakes that were added as feed to the batch reactor and samples of the spray dried soy powder were analyzed for various properties. The result of these properties for the soy flakes and for the spray dried soy powder are provided in Table 2 below:

TABLE 2

| PROPERTY | SOY FLAKES | SPRAY DRIED |
|---|---|---|
| Dry matter (weight %) | 96.25 | 94.77 |
| Organic matter (weight %, based on dry matter weight) | 92.41 | 89.53 |
| Ash (weight %, based on dry matter weight) | 7.59 | 10.47 |
| Crude protein (weight %, based on dry matter weight) | 49.41 | 45.96 |
| CP (weight %, based on organic matter weight) | 53.46 | 51.33 |
| Soluble protein (weight %, based on crude protein weight) | 66.50 | 85.10 |
| Immunoreactive glycinin (mg/g Crude Protein) | 469 | 227.3 |
| Immunoreactive β-conglycinin (mg/g Crude Protein) | 302 | 0.046 |
| Glycinin + β-conglycinin (mg/g Crude Protein) | 771 | 227 |

The weight percent of dry matter, organic matter, ash, crude protein, and crude protein in the soy flakes and in the spray dried soy powder were determined in accordance with the procedures for these variables set forth above in the Property Determination & Characterization Technique section. The glycinin and β-conglycinin concentrations in the soy flakes and in the spray dried soy powder were determined in accordance with the Glycinin and β-conglycinin Determinations technique that is described above in the Property Determination & Characterization Techniques section.

The results shown in Table 2 demonstrate that, even though the soy flakes used as feed in this example contained little, if any, denatured protein, enzymatic hydrolysis in accordance with the present invention was nonetheless effective to increase the concentration of soluble protein by about 28 percent in the spray dried soy powder, as compared to the concentration of soluble protein in the soybean flakes used as feed. Also, the enzymatic hydrolysis procedure decreased the glycinin concentration by about 51.5 percent in the spray dried soy powder, as compared to the glycinin concentration in the soy flakes used as feed. Additionally, the enzymatic hydrolysis reduced the concentration of β-conglycinin by about 99.9 percent in the spray dried soy powder, as compared to the concentration of β-conglycinin in the soy flakes used as feed. Consequently, the enzymatic hydrolysis was effective to reduce the concentrations of the principal antigenic proteins (glycinin plus β-conglycinin) by about 70.5 percent in the spray dried soy powder, as compared to the concentrations of the principal antigenic proteins (glycinin plus β-conglycinin) in the soy flakes used as feed.

Figure 2:
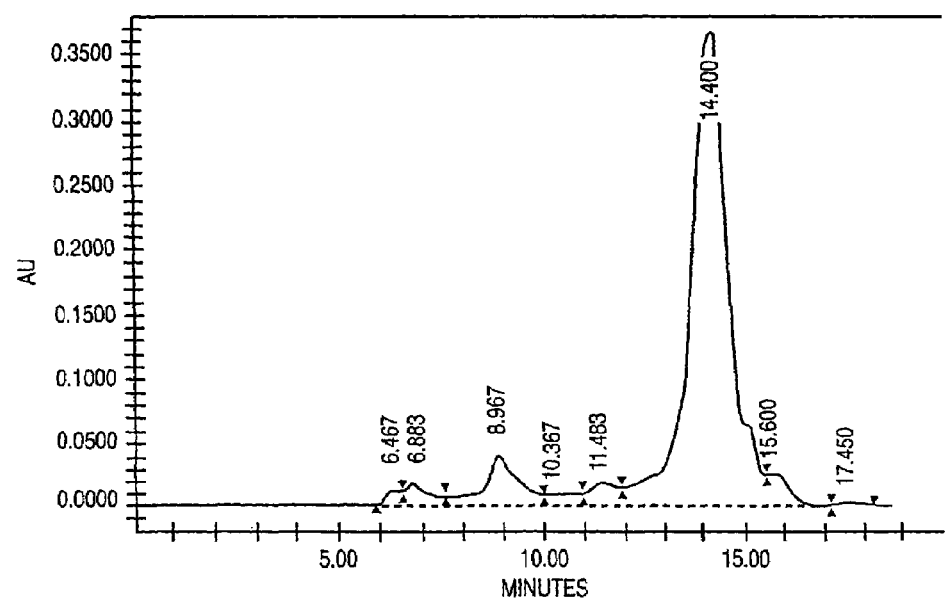
FIG. 2 is a size distribution plot of protein fragments with different molecular weights present in a vegetable protein product produced by the process of the present invention based upon the feed material of FIG. 1.

Additionally, the soy flakes and the spray dried soy powder were analyzed by high pressure liquid chromatography (HPLC) to detect any shift in molecular weight distribution of protein fragments in the spray dried soy powder versus the soy flakes that were used as feed. The high pressure liquid chromatography analysis was conducted in accordance with the procedure set forth above in the Property Determination & Characterization Techniques section. The HPLC results for the soy flakes are provided in the graph of FIG. 1, and the HPLC results for the spray dried soy powder are provided in the graph of FIG. 2. Details showing the variables used in determining the peak areas and the peak area values of each of the nine peaks shown in the graph of FIG. 1 and for the eight peaks shown in the graph of FIG. 2 are provided below in Tables 3 and 4, respectively.

TABLE 3

| Peak No. | Retention Time (min) | Area (uV × sec) | Height (uV) | % Area | % Height |
|---|---|---|---|---|---|
| 1 | 6.893 | 1998958 | 54950 | 9.47 | 10.00 |
| 2 | 7.577 | 747017 | 34379 | 3.54 | 6.25 |
| 3 | 8.493 | 3503407 | 80267 | 16.60 | 14.60 |
| 4 | 9.393 | 1717441 | 43824 | 8.14 | 7.97 |
| 5 | 10.327 | 710860 | 14281 | 3.37 | 2.60 |
| 6 | 11.727 | 177366 | 5774 | 0.84 | 1.05 |
| 7 | 12.377 | 514409 | 14148 | 2.44 | 2.57 |
| 8 | 13.293 | 538726 | 23503 | 2.55 | 4.28 |
| 9 | 14.243 | 11193027 | 278605 | 53.04 | 50.68 |

TABLE 4

| Peak No. | Retention Time (min) | Area (uV × sec) | Height (uV) | % Area | % Height |
|---|---|---|---|---|---|
| 1 | 6.467 | 304828 | 12772 | 1.06 | 2.62 |
| 2 | 6.883 | 695246 | 17243 | 2.41 | 3.53 |
| 3 | 8.967 | 2113479 | 37925 | 7.33 | 7.77 |
| 4 | 10.367 | 558318 | 9941 | 1.94 | 2.04 |
| 5 | 11.483 | 778394 | 17172 | 2.70 | 3.52 |
| 6 | 14.400 | 23445185 | 365929 | 81.29 | 74.97 |
| 7 | 15.600 | 897585 | 25413 | 3.11 | 5.21 |
| 8 | 17.450 | 49551 | 1728 | 0.17 | 0.35 |

The graphs of FIGS. 1 and 2 maybe readily interpreted when it is recognized that protein fragments with larger molecular weights show up earlier during the HPLC scan in peaks with shorter retention times and protein fragments with smaller molecular weights show up later during the HPLC scan in peaks with longer retention times. Thus, in the graph of FIG. 2, as compared to the graph of FIG. 1, there was a shift to larger peak areas at higher retention time as compared to peak areas at similar retention times in the graph of FIG. 1. This demonstrates that the spray dried soy powder, as represented in the graph of FIG. 2, contained protein fragments with a smaller molecular weight average and profile as compared to the soy flakes depicted in the graph of FIG. 1. This correlates well with the substantially enhanced soluble protein concentration in the spray dried soy powder, as compared to the soluble protein concentration in the soy flakes.

Example 2

This example demonstrates the effectiveness of the process of the present invention for substantially enhancing the protein dispersability index (PDI) of defatted soy flour with a PDI of about 20 that contained a substantial amount of denatured protein. This example demonstrates the effectiveness of the process of the present invention for substantially decreasing the concentration of antigenic proteins, such as glycinin and β-conglycinin, in the 20 PDI defatted soy flour.

In this example, the 20 PDI soy flour was HONEYSOY® 20 PDI soy flour that was obtained from Harvest States Oilseed Processing & Refining of Mankato, Minn. The 20 PDI soy flour was combined with warm tap water (50° C.) in several batches at the rate of about 2 pounds (907 grams) of 20 PDI flour per gallon (3.78 liters) of warm tap water. Each batch of 20 PDI soy flour was processed in a Model No. LTDW liquefier obtained from Breddo Likwifier of Kansas City, Kans. to liquify and slurry the mixture of 20 PDI soy flour and water.

Each batch of liquified soy flour/water slurry was transferred from the liquefier into a 250 gallon (946 liter) batch reactor that was identical to the 250 gallon (946 liter) batch reactor described in Example 1 above. A total of 325 pounds (147.4 kilograms) of the 20 PDI soy flour was combined with a total of 162.5 gallons (615.1 liters) of water in the soy flour/water slurry that was placed in the batch reactor. After addition of the 20 PDI soy flour and water to the batch reactor was completed, hot water was circulated through the jacket of the batch reactor to raise the temperature of the soy flour/water slurry to about 56.7° C. The initial pH of the soy flour/water slurry was about 6.67 standard pH units, and the initial Brookfield viscosity of the soy flour/water slurry was about 1240 centipoise at 56.7° C.

About 16 liters of a aqueous solution of 10 weight percent NaOH in water, based on the total weight of the sodium hydroxide solution, was added to the soy flour/water slurry to adjust the pH of the soy flour/water slurry to about 9.05 standard pH units. Then, about 3.3 pounds (about 1.5 kilograms) {about 1.65 liters} of the MULTIFECT® P-3000 enzyme composition was added to the soy flour/water slurry in the batch reactor. Thus, the MULTIFECT® P-3000 enzyme composition was added at a ratio of about one pound (about 454 grams) of the MULTIFECT® P-3000 enzyme composition per one hundred pounds (45.35 kilograms) of 20 PDI soy flour. After addition of the enzyme solution, the temperature of the soy flour/water slurry was determined to be about 56.7° C. and the Brookfield viscosity of the soy flour/water slurry was determined to be about 1900 centipoise at the 56.7° C. slurry temperature.

The enzymatic hydrolysis reaction triggered by addition of the MULTIFECT® P-3000 enzyme composition was allowed to continue in the batch reactor for a period of about 2 hours while maintaining the soy flour/water slurry at a temperature ranging from about 56.7° C. to about 60° C. No caustic or acid was added to the slurry during the enzymatic hydrolysis, and the pH of the slurry was observed to drop to about 7.58 standard pH units after the two-hour period of enzymatic hydrolysis. The pH, viscosity, and temperature of the soy flour/water slurry at various times during the two-hour enzymatic hydrolysis reaction are shown in Table 5 below:

TABLE 5

| Description | Time (minutes) | pH | Viscosity (cp) | Temp (° C.) |
| --- | --- | --- | --- | --- |
| Start of Enzymatic Hydrolysis | 0 | 9.05 | 1900 | 56.7 |
| | 5 | 8 | 200 | 57.3 |
| | 15 | 7.9 | 150 | 58.5 |
| | 30 | 7.77 | 110 | 58.6 |
| | 60 | 7.47 | 110 | 59 |
| | 90 | 7.64 | 120 | 59.3 |
| End of Enzymatic Hydrolysis | 120 | 7.58 | 80 | 60 |

Thus, the enzymatic hydrolysis reaction caused the Brookfield viscosity of the slurry to fall from about 1900 centipoise, measured at 56.7° C., to about 80 centipoise, measured at about 60° C.

After the two hour enzymatic hydrolysis period, steam was sent through the jacket of the batch reactor to inactivate the alkaline proteolytic enzymes. As the slurry was being heated, several Brookfield viscosity determinations were made. At 70° C., the Brookfield viscosity of the viscosity was found to be about 110 centipoise, at 80° C. the Brookfield viscosity of the slurry was found to be about 280 centipoise, and at 90° C. the Brookfield viscosity of the slurry was found to be about 440 centipoise. After reaching 90° C., the slurry was held at the temperature of about 90° C. to about 95° C. for a period of about 10 minutes to complete inactivation of the alkaline proteolytic enzyme. After the 10 minute enzyme inactivation period, the Brookfield viscosity of the slurry was determined to be about 420 centipoise at 90° C. and about 850 centipoise at room temperature (about 70° F.).

After enzyme inactivation was completed, the slurry was cooled and comminution in similar fashion to the cooling and comminution described in Example 1 and was thereafter spray dried using a vertical spray dryer obtained from C. E. Rogers Co. to produce spray dried soy flour. The recovery rate for the processing described above in this example was about 93.5%, since 325 pounds (147.42 kilograms) of 20 PDI soy flour were introduced into the batch reactor, and 304 pounds (137.9 kilograms) of spray dried soy flour were recovered from the spray dryer.

Example 3

This example is similar to Example 2 and consequently demonstrates the capabilities of the process of the present invention for substantially enhancing the Protein Dispersability Index (PDI) of defatted soy flour with a PDI of about 20 that contains a substantial amount of denatured protein and for substantially decreasing the content of antigenic proteins, such as glycinin and β-conglycinin in the 20 PDI defatted soy flour.

HONEYSOY® 20 PDI soy flour was used as the feed material in this example as in Example 2. Slurry containing the same ratio of 20 PDI soy flour to water was prepared and liquified as described in Example 2 and placed in a batch reactor that was identical to the batch reactor used in Example 2. A total of 175 pounds (79.4 kilograms) of 20 PDI soy flour was combined with a total of 87.5 gallons (331.3 liters) of water in the soy flour/water slurry that was placed in the batch reactor. After addition of the 20 PDI soy flour and water to the batch reactor was completed, hot water was circulated through the jacket of the batch reactor to raise the temperature of the soy flour/water slurry to about 54° C. The initial pH of the slurry in the batch reactor was about 6.56 standard pH units, and the initial Brookfield viscosity of the slurry was about 2800 centipoise at a slurry temperature of about 54° C. About one hour after preparation, while still being agitated, the pH of the slurry was observed to have dropped to about 6.2 standard pH units.

About 8.5 liters of the 10 weight percent NaOH aqueous solution was added to the slurry to adjust the pH of the slurry to about 9.06 standard pH units. Then, about 1.6 pounds (725.7 grams) {about 0.8 liters} of the MULTIFECT® P-3000 enzyme composition was added to the soy flour/water slurry in the batch reactor. Thus, the MULTIFECT® P-3000 enzyme composition was added at a ratio of about one pound (454 grams) of the MULTIFECT® P-3000 enzyme composition per one hundred pounds (45.35 kilograms) of 20 PDI soy flour. After addition of the enzyme solution, the temperature of the soy flour/water slurry was determined to be about 53.9° C. and the Brookfield viscosity of the soy flour/water slurry was determined to be about 1730 centipoise at the 53.9° C. slurry temperature.

The enzymatic hydrolysis reaction triggered by an addition of the MULTIFECT® P-3000 enzyme composition was allowed to continue in the batch reactor for a period of about 2 hours while maintaining the soy flour/water slurry at a temperature ranging from about 54° C. to about 60° C. No caustic or acid was added to the slurry during the enzymatic hydrolysis, and the pH of the slurry was observed to drop to about 7.21 standard pH units after the two-hour period of enzymatic hydrolysis. The pH, viscosity, and temperature of the soy flour/water slurry at various times during the two-hour enzymatic hydrolysis reaction are shown in Table 6 below:

TABLE 6

| Description | Time (minutes) | pH | Viscosity (centipoise) | Temp (° C.) |
|---|---|---|---|---|
| Start of Enzymatic Hydrolysis | 0 | 9.06 | 1730 | 53.9 |
| | 5 | 7.58 | 220 | 54.8 |
| | 60 | 7.31 | 80 | 58.8 |
| | 90 | 7.26 | 60 | 59.2 |
| End of Enzymatic Hydrolysis | 120 | 7.21 | 60 | 59.2 |

Thus, the enzymatic hydrolysis reaction caused the Brookfield viscosity of the slurry to fall from about 1730 centipoise, measured at 53.9° C., to about 60 centipoise, measured at about 59.2° C.

After the two-hour enzymatic hydrolysis period, steam was entered into the jacket of the batch reactor to inactivate the alkaline proteolytic enzymes. After reaching 90° C. the soy flour/water slurry was held at the temperature of about 90° C. to about 95° C. for a period of about 10 minutes to complete inactivation of the alkaline proteolytic enzyme.

Discussion of Results for Examples 2 and 3

Figure 3:
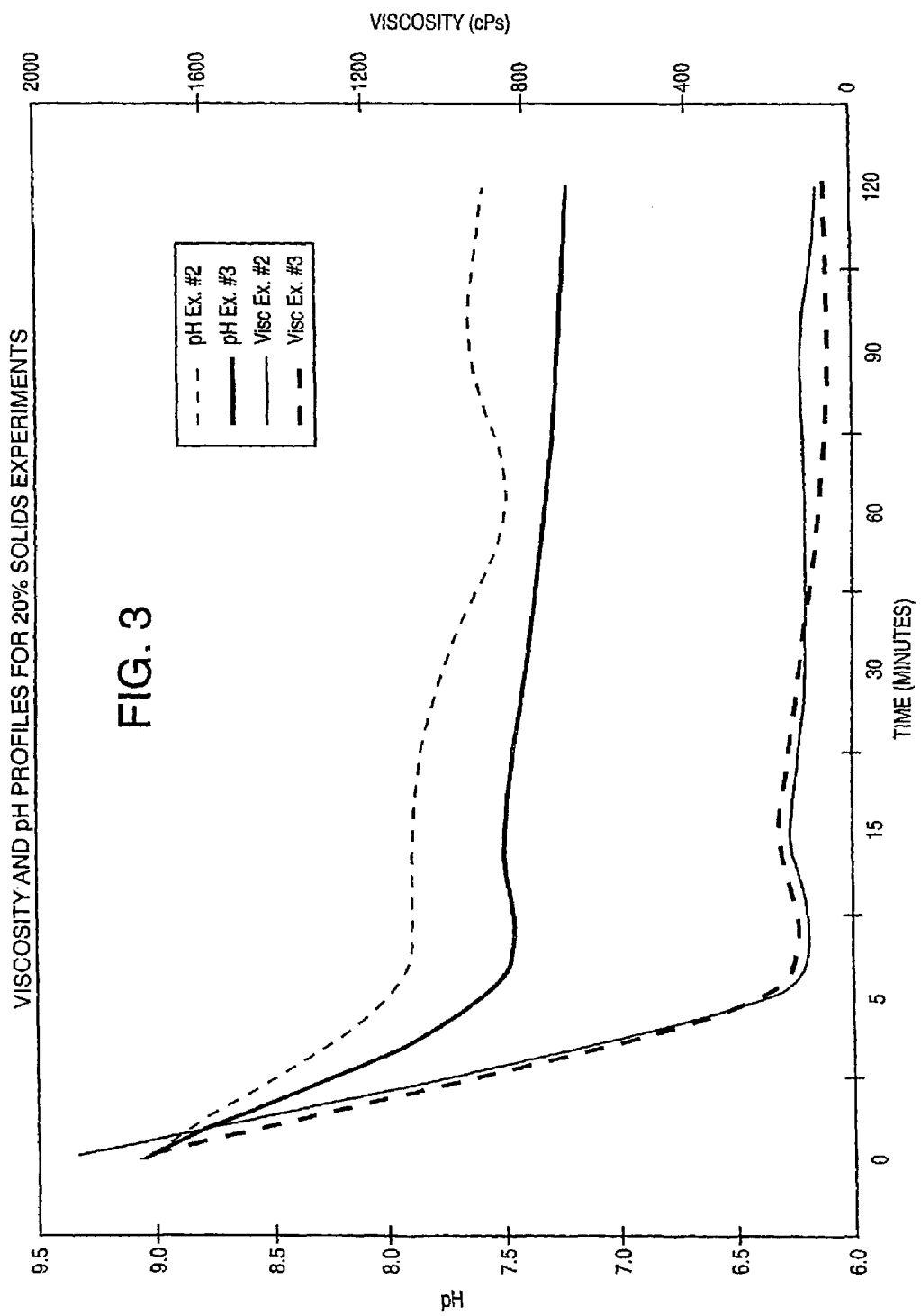
FIG. 3 is a plot of pH and viscosity profiles of a pair of different slurries based on vegetable protein sources during enzymatic hydrolysis of the slurries in accordance with the present invention.

Examples 2 and 3 each used the same 20 PDI defatted soy flour as the feed material upon which enzymatic hydrolysis was conducted. Examples 2 and 3 each used the same ratio of 20 PDI defatted soy flour to water in the slurry that was enzymatically hydrolyzed. Examples 2 and 3 each used the same alkaline agent and arrived at approximately the same pH both before and after addition of the alkaline agent and the enzyme solution. Also, Examples 2 and 3 each used the same MULTIFECT® P-3000 enzyme composition, and the same weight ratio of the MULTIFECT® P-3000 enzyme composition to 20 PDI soy flour ratio was used in both Examples 2 and 3. A graph that is included as FIG. 3 illustrates how the pH profiles of the slurry during the enzymatic hydrolysis reactions track in very similar fashion for both Examples 2 and 3. This graph of FIG. 3 also illustrates how the viscosity profiles of the slurry during the enzymatic hydrolysis reactions track in very similar fashion for both Examples 2 and 3. It is noted that the viscosities plotted in FIG. 3 were not corrected to a standard temperature, but were instead determined at the temperature of the slurry at the time of sampling.

Samples of the 20 PDI soy flour used as the feed material to be hydrolyzed in Examples 2 and 3 above were collected and blended in preparation for analysis. The blended 20 PDI soy flour sample and samples of the spray dried soy flour obtained in Examples 2 and 3 were analyzed for various properties. The results of these analyses are provided in Table 7 below:

TABLE 7

| PROPERTY | SOY FLOUR | EXAMPLE 2 SPRAY DRIED SOY FLOUR | EXAMPLE 3 SPRAY DRIED SOY FLOUR |
|---|---|---|---|
| Dry matter (weight %) | 94.0 | 94.5 | 93.9 |
| Organic matter (weight %, based on dry matter weight) | 93.3 | 92.1 | 92.3 |
| Ash (weight %, based on dry matter weight) | 6.7 | 7.9 | 7.7 |
| Crude protein (weight %, based on dry matter weight) | 48.6 | 48.0 | 47.3 |
| CP (weight %, based on organic matter weight) | 52.1 | 52.1 | 51.2 |
| Soluble protein (weight %, based on crude protein weight) | 20.8 | 78.4 | 81.5 |
| Immunoreactive glycinin (mg/g Crude Protein) | 71 | 7.5 | 21 |
| Immunoreactive β-conglycinin (mg/g Crude Protein) | 32 | 0 | 0 |
| Glycinin + β-conglycinin (mg/g Crude Protein) | 103 | 7.5 | 21 |

The weight percent of dry matter, organic matter, ash, crude protein, and crude protein in the 20 PDI soy flour and in the spray dried soy flour were determined in accordance with the procedures for these variables set forth above in the Property Determination & Characterization Technique section. The glycinin and β-conglycinin concentrations in the 20 PDI soy flour and in the spray dried soy flour were determined in accordance with the Glycinin and β-conglycinin Determinations technique that is described above in the Property Determination & Characterization Techniques section.

The results shown in Table 7 demonstrate that the enzymatic hydrolysis procedures that were carried out in Examples 2 and 3 were each effective to dramatically improve the PDI of the blended 20 PDI soy flour from a PDI of about 20 all the way up to a PDI on the order of about 80 for the spray dried soy flour, specifically, a PDI of 78.4 for Example 2 and a PDI of 81.5 for Example 3. Thus, the enzymatic hydrolysis of Example 2 improved the PDI in the spray dried soy flour by about 277 percent, as compared to the 20 PDI soy flour, whereas the enzymatic hydrolysis of Example 3 improved the PDI in the spray dried soy flour by about 292 percent, as compared to the 20 PDI soy flour. These dramatic increases in the PDI values for soy flours treated in accordance with the present invention graphically illustrate the ability of the present invention to improve solubilities of vegetable protein matter, such as those containing denatured soy proteins.

Also, the enzymatic hydrolysis procedures of Examples 2 and 3 effected dramatic decreases in the concentration of one antigenic protein, glycinin. In Example 2, the glycinin concentration in the spray dried soy flour was about 89 percent less than the glycinin level in the 20 PDI soy flour, whereas in Example 3 the decrease in glycinin concentration for the spray dried soy flour was a more modest 70 percent, as compared to the glycinin concentration in the 20 PDI soy flour. The inventive enzymatic hydrolysis process was even more dramatic in its effectiveness at treating another antigenic protein, namely β-conglycinin. More specifically, in Examples 2 and 3, the enzymatic hydrolysis procedure was able to completely eliminate any β-conglycinin content in the spray dried soy flour produced in Examples 2 and 3, even though the 20 PDI soy flour used as feed in these examples had a β-conglycinin concentration of 32 milligrams per gram of crude protein. Consequently, in Example 2, the enzymatic hydrolysis was effective to reduce the overall concentration of the principal antigenic proteins (glycinin plus β-conglycinin) by nearly 90 percent in the spray dried soy powder, as compared to the concentration of the principal antigenic proteins in the 20 PDI soy flour. Likewise, the enzymatic hydrolysis was effective to reduce the concentration of the principal antigenic proteins (glycinin plus β-conglycinin) by about 80 percent in the spray dried soy flour of Example 3, as compared to the concentration of the principal antigenic proteins in the 20 PDI soy flour.

Samples of a blend of the 20 PDI soy flour used in Examples 2 and 3 as the feed material and samples of a blend of the spray dried soy flour produced in Examples 2 and 3 were analyzed by high pressure liquid chromatography (HPLC) to detect any shift in the spray dried soy flour toward protein fragments with smaller molecular weights versus the 20 PDI soy flour. The high pressure liquid chromatography analysis was conducted in accordance with the procedure set forth above in the Property Determination & Characterization Techniques section. The HPLC results for the blend of 20 PDI soy flour used as feed in Examples 2 and 3 are provided in the graph of FIG. 4, and the HPLC results for blend of spray dried soy flour from Examples 2 and 3 are provided in the graph of FIG. 5.

Figure 4:
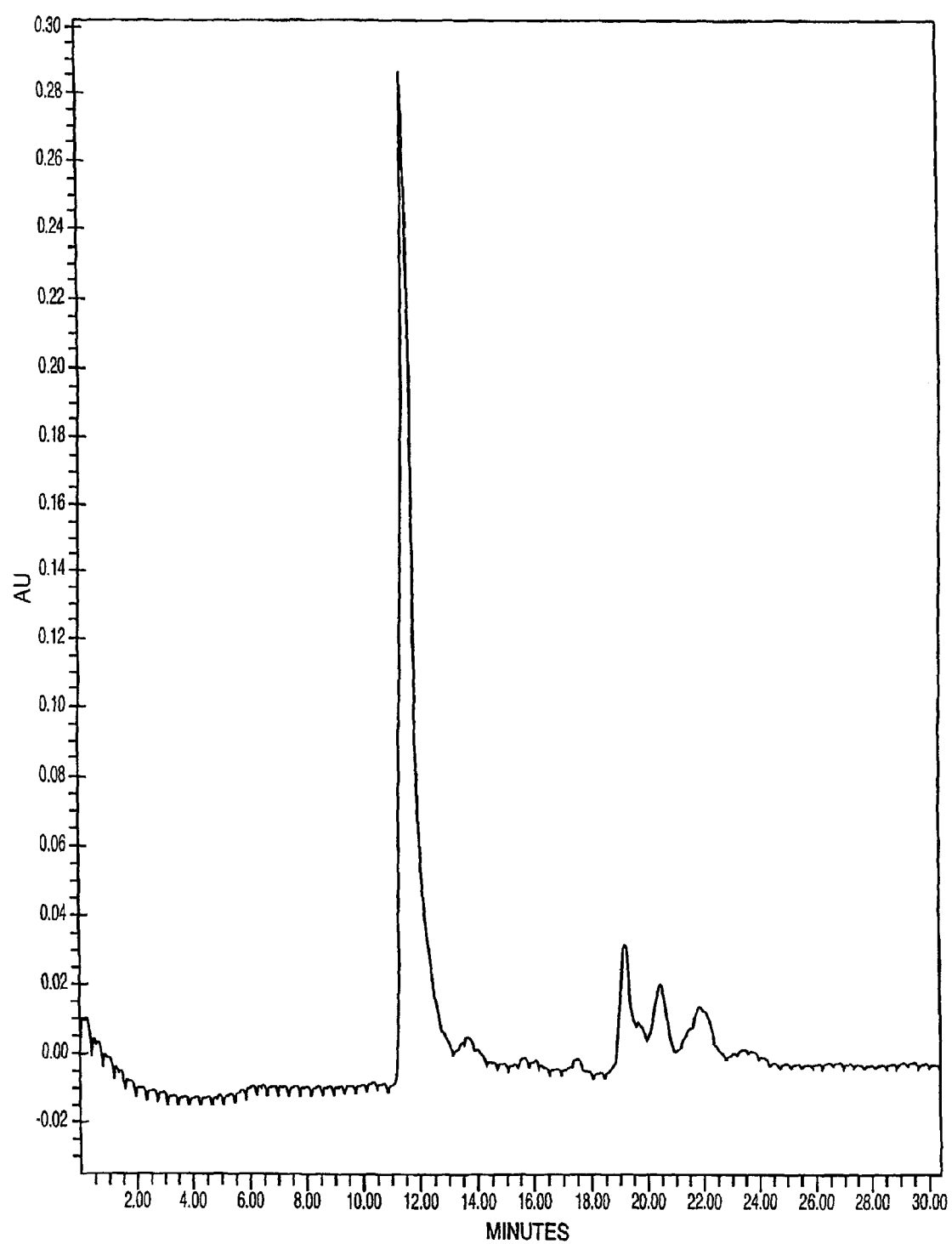
FIG. 4 is a size distribution plot of protein fragments with different molecular weights present in another vegetable protein source that was used as feed material in the process of the present invention.
Figure 5:
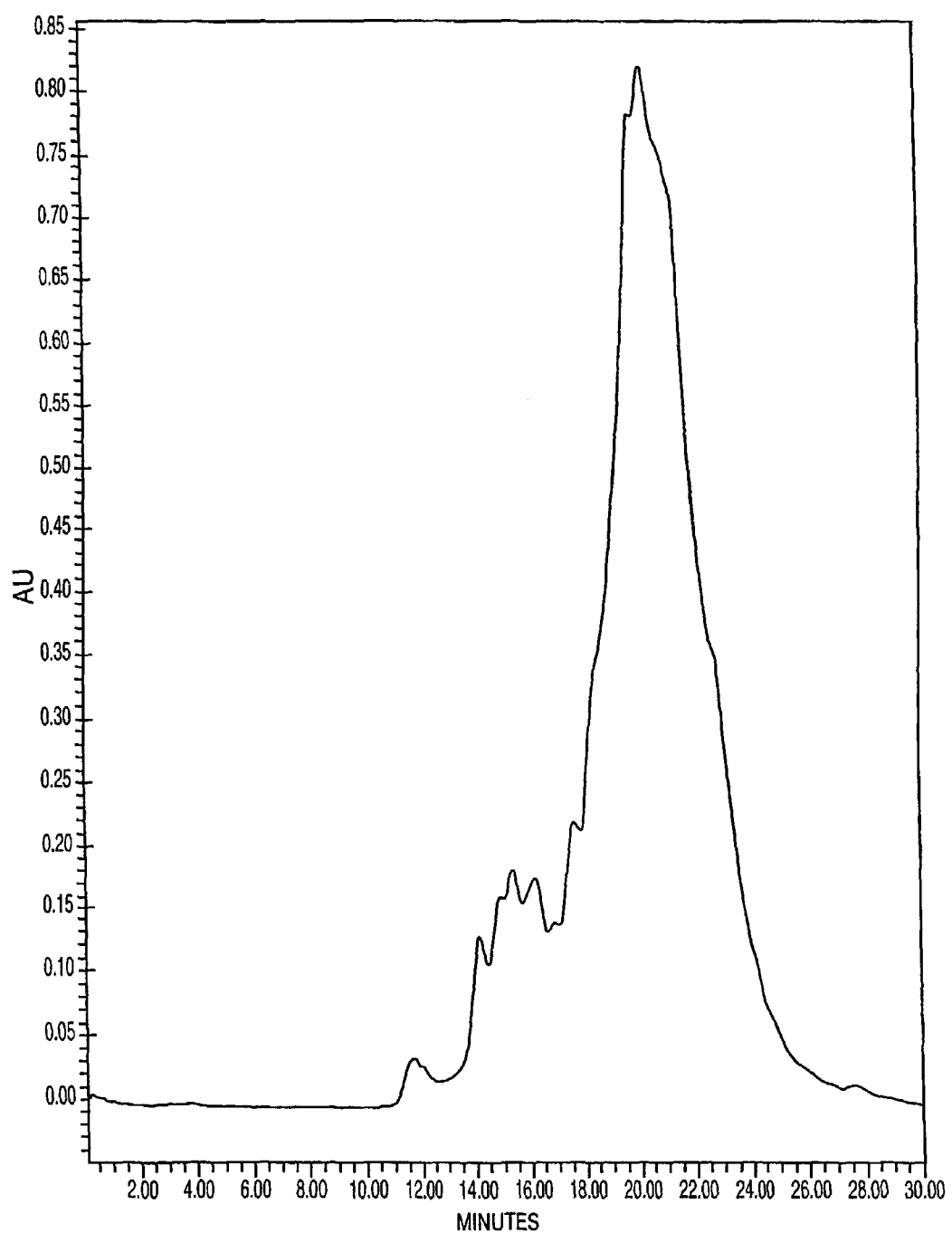
FIG. 5 is a size distribution plot of protein fragments with different molecular weights present in a vegetable protein product produced by the process of the present invention based upon the feed material of FIG. 4.

The graphs of FIGS. 4 and 5 may be readily interpreted when it is recognized that protein fragments with larger molecular weights show up earlier during the HPLC scan in peaks with shorter retention times and protein fragments with smaller molecular weights show up later during the HPLC scan in peaks with longer retention times. Thus, in the graph of FIG. 5, as compared to the graph of FIG. 4, there was a shift to larger peak areas at higher retention times as compared to peak areas at similar retention times in the graph of FIG. 4. This demonstrates that the blend of spray dried soy flours produced in Examples 2 and 3, as represented in the graph of FIG. 5, contained protein fragments with a smaller molecular weight average and profile, as compared to the sample of blended 20 PDI soy flour feed material from Examples 2 and 3, as depicted in the graph of FIG. 4. This correlates well with the substantially enhanced soluble protein concentration (increased PDI) in the spray dried soy flour samples of Examples 2 and 3, as compared to the soluble protein concentration in the 20 PDI soy flours used as feed in Examples 2 and 3.

The graphs of FIGS. 4 and 5, when subject to a regression analysis, further demonstrate the beneficial protein molecular weight reduction achieved by the process of the present invention. Specifically, this regression analysis revealed that the sample of blended 20 PDI soy flour feed material from Examples 2 and 3, as depicted in the graph of FIG. 4, includes mostly protein fragments with a molecular weight size ranging from about 123 kilodaltons to about 394 kilodaltons. On the other hand, regression analysis revealed that the blend of spray dried soy flours produced in Examples 2 and 3, as represented in the graph of FIG. 5, includes mostly protein fragments with a molecular weight size below about 2400 Daltons, with the actual range extending from about 200 Daltons to about 2400 Daltons for the vast majority of the protein fragments.

Although the present invention has been described with reference to preferred embodiments, workers skilled in the art will recognize that changes may be made in form and detail without departing from the spirit and scope of the invention.

The invention claimed is:

1. A method of treating a proteinaceous soybean material to be utilized in an animal feed and having a first combined concentration of β-conglycinin and glycinin, the method comprising:
   combining the proteinaceous soybean material with an alkaline proteinase from *Bacillus amyloliquefaciens* to form a reaction mixture consisting of a single stage reaction wherein the single stage reaction period begins when the reaction mixture is formed, the reaction mixture initially having a pH of at least about 7.0 standard pH units and wherein the reaction period is about five minutes to about two hours;
   allowing the alkaline proteinase to hydrolyze the glycinin and β-conglycinin present in the reaction mixture at a temperature of about 60° C. or less to form a proteinaceous intermediate; and
   inactivating the alkaline proteinase present in the reaction mixture, defining an end of the single stage reaction period, under conditions sufficient to form a proteinaceous product, having a second combined concentration of β-conglycinin and glycinin, which is at least 92 percent less than the first combined concentration of β-conglycinin and glycinin.

2. The method of claim 1 wherein the reaction mixture initially has a pH of at least about 8.5 standard pH units.

3. The method of claim 2 wherein the method is effective to provide a second concentration of β-conglycinin that is at least 99 percent less than the first concentration of β-conglycinin when no pH adjustment is made during the reaction period after initiation of the hydrolysis.

4. The method of claim 1 wherein the reaction mixture initially has a pH greater than about 8.5 standard pH units.

5. The method of claim 1 wherein the second concentration of β-conglycinin is about 100 percent less than the first concentration of β-conglycinin.

6. The method of claim 1 wherein the *Bacillus amyloliquefaciens* is a recombinant subtilisin.

7. A method of treating a proteinaceous soybean material to be utilized in an animal feed and having a first concentration of glycinin and a first concentration of β-conglycinin, the method comprising:

combining the proteinaceous soybean material with a serine proteinase from *Bacillus amyloliquefaciens* to form a reaction mixture consisting of a single stage reaction wherein the single stage reaction period begins when the reaction mixture is formed, the reaction mixture initially having a pH of at least about 7.0 standard pH units and wherein the reaction period is about five minutes to about two hours;

allowing the serine proteinase to hydrolyze the glycinin and β-conglycinin present in the reaction mixture at a temperature of about 60° C. or less to form a proteinaceous intermediate; and inactivating the serine proteinase present in the reaction mixture, defining an end of the single stage reaction period, under conditions sufficient to form a proteinaceous product, having a second concentration of glycinin and β-conglycinin, the second concentration of glycinin being greater than about 50 percent less than the first concentration of glycinin, and the second concentration of β-conglycinin being at least about 99 percent less than the first concentration of β-conglycinin.

8. The method of claim 7 wherein the reaction mixture initially has a pH of at least about 8.5 standard pH units.

9. The method of claim 8 wherein the method is effective to provide the second concentration of glycinin that is at least about 50 percent less than the first concentration of glycinin when no pH adjustment is made during the reaction period after initiation of the hydrolysis.

10. The method of claim 7 wherein the reaction mixture initially has a pH greater than about 8.5 standard pH units.

11. The method of claim 7 wherein the second concentration of glycinin is at least about 70 percent less than the first concentration of glycinin.

12. The method of claim 7 wherein the *Bacillus amyloliquefaciens* is a recombinant subtilisin.

13. A method of treating a proteinaceous soybean material to be utilized in an animal feed and having a first Protein Dispersability Index, the method comprising:

combining the proteinaceous soybean material with an alkaline proteinase from *Bacillus amyloliquefaciens* to form a reaction mixture consisting of a single stage reaction, wherein the proteinaceous soybean material has an average protein molecular weight of about 125 kilodaltons to about 440 kilodaltons, wherein the single stage reaction period begins when the reaction mixture is formed, the reaction mixture initially having a pH of at least about 7.0 standard pH units and wherein the reaction is about five minutes to about two hours;

allowing the alkaline proteinase to hydrolyze protein present in the reaction mixture at a temperature of about 60° C. or less to form a proteinaceous intermediate; and inactivating the alkaline proteinase present in the reaction mixture, defining an end of the single stage reaction period, under conditions sufficient to form a proteinaceous product, having a second Protein Dispersability Index, at least about 20 percent greater than the first Protein Dispersability Index and wherein the proteinaceous product has an average protein molecular weight of about 7500 daltons or less.

14. The method of claim 13 wherein the first Protein Dispersability Index is at least about 60 percent.

15. The method of claim 13 wherein the first Protein Dispersability Index is about 20 percent, or less, and the second Protein Dispersability Index is at least about 70 percent.

16. The method of claim 13 wherein the proteinaceous product has an average protein molecular weight of about 2500 Daltons or less.

17. The method of claim 13 wherein the reaction mixture initially has a pH of at least about 8.5 standard pH units.

18. The method of claim 17 wherein the first Protein Dispersability Index is about 20 percent, or less, the method effective to make the second Protein Dispersability Index at least about 70 percent when no pH adjustment is made during the reaction period after initiation of the hydrolysis.

19. The method of claim 13 wherein the reaction mixture initially has a pH greater than about 8.5 standard pH units.

20. The method of claim 19 wherein the first Protein Dispersability Index is about 20 percent, or less, and the second Protein Dispersability Index is at least about 70 percent.

21. The method of claim 13 wherein the *Bacillus amyloliquefaciens* is a recombinant subtilisin.

22. A method of treating a proteinaceous soybean material to be utilized in an animal feed and having an initial Protein Dispersibility Index, the method consisting essentially of:

combining the proteinaceous material with water to form a slurry, the proteinaceous material having a first concentration of glycinin and a first concentration of β-conglycinin;

adjusting the pH of the slurry to greater than about 8.5 standard pH units;

combining a serine proteinase with the slurry, defining the beginning of a single stage reaction period; and permitting the serine proteinase to hydrolyze protein contained in the slurry to form a proteinaceous product at a temperature of about 60° C. or less until the proteinase is inactivated, defining an end to the single stage reaction, the proteinaceous product having a second concentration of glycinin greater than about 50 percent less than the first concentration of glycinin, and a second concentration of β-conglycinin at least about 99 percent less than the first concentration of β-conglycinin, the proteinaceous product having a second Protein Dispersability Index of at least about 20 percent greater than the initial Protein Dispersability Index rate.

23. The method of claim 22 wherein the pH of the slurry is adjusted to a pH within the range of about 9.0 standard pH units to about 9.5 standard pH units.

24. The method of claim 22 wherein only a single stage hydrolysis reaction occurs in the slurry and no pH adjustment is made to the slurry after the serine proteinase is combined with the slurry.

25. A method of treating a proteinaceous soybean material to be utilized in an animal feed, the method consisting essentially of:
- combining the proteinaceous soybean material having a first concentration of β-conglycinin and a first concentration of glycinin with an alkaline proteinase from *Bacillus amyloliquefaciens* to form a reaction mixture consisting of a single stage reaction wherein the reaction period begins when the reaction mixture is formed, the reaction mixture initially having a pH of at least about 7.0 standard pH units;
- allowing the proteinase to hydrolyze protein present in the reaction mixture at a temperature of about 60° C. or less to form a proteinaceous intermediate; and
- inactivating the enzyme present in the reaction mixture, defining an end of the reaction period, under conditions sufficient to form a proteinaceous product having a concentration of β-conglycinin that is at least 99 percent less than the first concentration of β-conglycinin and having a concentration of glycinin that is at least 70 percent less than the first concentration of glycinin, the proteinase derived from a genetically modified strain of *Bacillus amyloliquefaciens*.

26. A method of treating a proteinaceous soybean material to be incorporated into an animal feed, the method consisting essentially of:
- combining the proteinaceous soybean material with an alkaline proteinase from *Bacillus amyloliquefaciens* to form a reaction mixture consisting of a single stage reaction, wherein the proteinaceous soybean material has an average protein molecular weight of about 125 kilodaltons to about 440 kilodaltons, wherein the single stage reaction period begins when the reaction mixture is formed, the reaction mixture initially having a pH of at least about 7.0 standard pH units;
- allowing the proteinase to hydrolyze protein present in the reaction mixture at a temperature of about 60° C. or less to form a proteinaceous intermediate; and
- inactivating the proteinase present in the reaction mixture, defining an end of the single stage reaction period, under conditions sufficient to form a proteinaceous product, having an average protein molecular weight of about 7500 daltons or less.

27. The method of claim 26 wherein the proteinaceous material has a first concentration of β-conglycinin and the proteinaceous product has a second concentration of β-conglycinin, the second concentration of β-conglycinin being at least 99 percent less than the first concentration of β-conglycinin.

28. The method of claim 26 wherein the proteinase is expressed by a genetically modified strain of *Bacillus amyloliquefaciens*.

29. A method of treating a proteinaceous soybean material to be utilized as a component of an animal feed and having a first combined concentration of β-conglycinin and glycinin, the method consisting essentially of:
- combining the proteinaceous soybean material with a serine proteinase to form a reaction mixture consisting of single stage reaction wherein the single stage reaction period begins when the reaction mixture is formed, the reaction mixture initially having a pH of greater than about 8.5 standard pH units;
- allowing the proteinase to hydrolyze protein present in the reaction mixture at a temperature of about 60° C. or less to form a proteinaceous intermediate; and
- inactivating the proteinase present in the reaction mixture, defining an end of the single stage reaction period, under conditions sufficient to form a proteinaceous product, having a second combined concentration of β-conglycinin and glycinin being at least 70 percent less than the first combined concentration, the proteinase being produced from a recombinant derived *B. licheniformis*, *B. amyloliquefaciens*, or *B. subtilis*.

30. The method of claim 29 wherein the proteinaceous soybean material has a first concentration of β-conglycinin and the proteinaceous product has a second concentration of β-conglycinin, the second concentration of β-conglycinin being at least 99 percent less than the first concentration of β-conglycinin.

31. The method of claim 29 wherein the reaction mixture initially has a pH within the range of about 9.0 standard pH units to about 9.5 standard pH units.

* * * * *